(12) United States Patent
Willmann et al.

(10) Patent No.: US 7,351,546 B2
(45) Date of Patent: *Apr. 1, 2008

(54) FLOW CYTOMETRIC, WHOLE BLOOD DENDRITIC CELL IMMUNE FUNCTION ASSAY

(75) Inventors: Kerstin Willmann, Sunnyvale, CA (US); John F. Dunne, Pleasanton, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 663 days.

This patent is subject to a terminal disclaimer.

(21) Appl. No.: 10/635,972

(22) Filed: Aug. 7, 2003

(65) Prior Publication Data

US 2005/0079555 A1    Apr. 14, 2005

Related U.S. Application Data

(63) Continuation of application No. 09/787,092, filed as application No. PCT/US99/21731 on Sep. 21, 1999, now abandoned, which is a continuation-in-part of application No. 09/158,406, filed on Sep. 22, 1998, now Pat. No. 6,495,333.

(51) Int. Cl.
  *G01N 33/00*    (2006.01)
(52) U.S. Cl. ............ 435/7.24; 435/7.2; 435/40.5; 435/287.2; 435/962; 435/973; 436/10; 436/17; 436/63; 436/64; 436/164; 436/172; 436/177; 436/522; 436/546

(58) Field of Classification Search ........... 435/6, 435/7.2, 7.24, 325, 326, 335, 375, 962, 973, 435/40.5, 287.2; 436/63, 64, 164, 172, 177, 436/10, 17, 522, 546; 422/83
See application file for complete search history.

(56) References Cited

U.S. PATENT DOCUMENTS 4,654,312 A    3/1987    Chang et al.

(Continued)

FOREIGN PATENT DOCUMENTS

WO    WO 97/24438    7/1997

(Continued)

OTHER PUBLICATIONS

Olweus et al., Peripheral Blood Dendritic Cells Revealed by Flow Cytometry, Becton Dickinson—Application Note 3, (1998).*

(Continued)

*Primary Examiner*—Gailene Clare R. Gabel
(74) *Attorney, Agent, or Firm*—Douglas A. Petry

(57) ABSTRACT

The invention provides a flow cytometric method for measuring dendritic cell function in whole blood, comprising: (a) contacting a whole blood sample with a dendritic cell activator; (b) adding to the sample a plurality of dendritic cell-distinguishing antibodies and at least one cytokine-specific antibody; and then (c) flow cytometrically assaying the sample for the binding of the cytokine-specific antibody by at least one distinguishable DC subset. Other assays are presented in which DC activation markers are assessed.

15 Claims, 13 Drawing Sheets

U.S. PATENT DOCUMENTS

| | | | |
|---|---|---|---|
| 4,902,613 | A | 2/1990 | Chang et al. |
| 5,098,849 | A | 3/1992 | Hilerio et al. |
| 5,597,563 | A | 1/1997 | Beschorner |
| 5,627,025 | A | 5/1997 | Steinman et al. |
| 5,627,040 | A | 5/1997 | Bierre et al. |
| 5,643,786 | A | 7/1997 | Cohen et al. |
| 5,648,219 | A | 7/1997 | MacKay et al. |
| 5,648,248 | A | 7/1997 | Zenke et al. |
| 5,698,679 | A | 12/1997 | Nemazee |
| 5,788,963 | A | 8/1998 | Murphy et al. |
| 6,495,333 | B1* | 12/2002 | Willmann et al. .......... 435/7.24 |

FOREIGN PATENT DOCUMENTS

| | | |
|---|---|---|
| WO | WO 97/29183 | 8/1997 |
| WO | WO 98/15579 | 4/1998 |
| WO | WO 98/15615 | 4/1998 |

OTHER PUBLICATIONS

Becton Dickinson, Detection of Intracellular Cytokines in Activated Lymphocytes Application Note 1, (1996).*

Andersson, U. et al., "Enumeration of IFN-.gamma.-Producing Cells by Flow Cytometry," J. Immunological Methods, 112 (1) :139-142 (1988).

Banchereau, J. et al., "Dendritic Cells and the Control of Immunity," Nature, 392:245-252 (1998).

Becton Dickinson Immunocytometry Systems, "Detection of Intracellular Cytokines in Activated Lymphocytes," Application Note 1, Immune Function, 1-12 (1996).

Caux, C. et al., "CD34+ Hematopoietic Progenitors from Human Cord Blood Differentiate Along Two Independent Dendritic Cell Pathways in Response to GM-CSF+TNF.alpha.," J. Exp. Med., 184 (2): 695-706 (1996).

Caux, C. et al., "Tumor Necrosis Factor-alpha Strongly Potentiates Interleukin-3 and Granulocyte-Macrophage Colony-Stimulating Factor-Induced Proliferation of Human CD34.sup.+ Hematopoietic Progenitor Cells," Blood, 75 (12) :2292-2298 (1990).

deCaestecker, M.P. et al., "The Detection of Intracytoplasmic Interleukin-1.alpha., Interleukin-1.beta. and Tumor Necrosis Factor .alpha. Expression in Human Monocytes Using Two Colour Immunofluorescence Flow Cytometry," J. Immunological Methods, 154 (1) :11-20 (1992).

de Saint-Vis, B. et al., "The Cytokine Profile Expressed by Human Dendritic Cells Is Dependent on Cell Subtype and Mode of Activation," J. Immunology, 160:166-1676 (1998).

Ghanekar, S. et al., "Cytokine Expression by Human Peripheral Blood Dendritic Cells Stimulated In Vitro with HIV-1 and Herpes Simplex Virus," J. Immunology, 157 (9) :4028-4036 (1996).

Grouard, G. et al., "The Enigmatic Plasmacytoid T Cells Develop into Dendritic Cells with Interleukin (IL) -3 and CD40-Ligand," J. Exp. Med., 185 (6) :1101-1111 (1997).

Grouard, G. et al., "Role of Dendritic and Follicular Dendritic Cells in HIV Infection and Pathogenesis," Current Opinion in Immunology, 9 (4) :563-567 (1997).

Hallden, G. et al., "A New Membrane Permeabilization Method for the Detection of Intracellular Antigens by Flow Cytometry," J. Immunological Methods, 124 (1) :103-109 (1989).

Ingalls, R.R. et al., "CD11c/CD18, A Transmembrane Signaling Receptor for Lipopolysaccharide," J. Exp. Med., 181 (4) : 1473-1479, 1998.

Jacob, M.C. et al., "Membrane Cell Permeabilisation With Saponin and Mutiparametric Analysis by Flow Cytometry," Cytometry, 12 (6) :550-558 (1991).

Jung, T. et al., "Detection of Intracellular Cytokines by Flow Cytometry," J. Immunological Methods, 159:197-207 (1993).

Kabilan, L. et al., "Detection of Intracellular Expression and Secretion of Interferon-.gamma. at the Single-Cell Level After Activation of Human T Cells with Tetanus Toxoid In Vitro," European J. Immunology, 20 (5) :1085-1089 (1990).

Kahan, Mel, "Detecting Intracellular Cytokines in Activated Monocytes," Application Note 2, Immune Function, Becton Dickinson Immunocytometry Systems, 1-12 (1997).

Lore K. et al., "Immunocytochemical Detection of Cytokines and Chemokines in Langerhans Cells and In Vitro Derived Dendritic Cells," J. Immunological Methods, 214:97-111 (1998).

Macatonia, S.E. et al., "Dendritic Cells Produce IL-12 and Direct the Development of Th1 Cells from Naive CD4.sup.30 T Cells," J. Immunology, 154 (10):5071-5079 (1995).

Maino, V.C. et al., "Flow Cytometric Method for Analysis of Cytokine Expression in Clinical Samples," Clinical Immunology Newsletter, 16(6) :95-98 (1996).

O'Doherty, U. et al., "Human Blood Contains Two Subsets of Dendritic Cells, One Immunologically Mature and the Other Immature," Immunology, 82 (3) :487-493 (1994).

Olweus, J. et al., "Dendritic Cell Ontogeny: A Human Dendritic Cell Lineage of Myeloid Origin," Proc. Natl. Acad. Sci. USA, 94 (23) :12551-12556 (1997).

Picker, L.J. e al., "Direct Demonstration of Cytokine Synthesis Heterogeneity Among Human Memory/Effector T Cells by Flow Cytometry," Blood, 86 (4) :1408-1419 (1995).

Prussin, C., Cytokine Flow Cytometry: Assessing Cytokine Production at the Single Cell level, Clinical Immunology Newsletter, 16 (6) : 85-91 (1996).

Sander, B. et al., "Assessment of Cytokines by Immunofluorescence and the Paraformaldehyde-Saponin Procedure," Immunological Reviews, 119:65-93 (1991).

Scheinecker, C. et al., "Phenotypic, Morphological and Functional Analysis of CD11c.sup.+ and CD11c Human Peripheral Blood Dendritic Cells," ASH Meeting, San Diego, Dec. 1997.

Steinman, R.M. et al., "Identification of a Novel Cell Type in Peripheral Lymphoid Organs of Mice," J. Exper. Med., 137:1142-1162 (1973).

Steinman, R.M., "The Dendritic Cell System and its Role In Immunogenicity," Annu. Rev. Immunol., 9:271-296 (1991).

Suni, M.A. et al., "Detection of Antigen-Specific T Cell Cell Cytokine Expression in Whole Blood by Flow Cytometry," Journal of Immmunological Methods, 212:89-98 (1998).

Thomas, R. et al., "Human Peripheral Blood Dendritic Cell Subsets," J. Immunology, 153 (9) :4016-4028 (1994).

Vikingsson, A. et al., "Enumeration of IFN-.gamma. Producing Lymphocytes by Flow Cytometry and Correlation with Quantitative Measurement of IFN-.gamma.," J. Immunological Methods, 173 (2) : 219-228 (1994).

Waldrop, S.L. et al., "Determination of Antigen-specific Memory/Effector CD4.sup.+ T Cell Frequencies by Flow Cytometry," J. Clinical Investigation, 99 (7) :1739-1750 (1997).

Weissman, D. et al., "Role of Dendritic Cells in Immunopathogenesis of Human Immunodeficiency Virus Infection," Clinical Microbiology Reviews, 10 (2) :358-367 (1997).

Willmann, K. et al., "Peripheral Blood Dendritic Cells Revealed by Flow Cytometry," Application Note 3, Reagents, Becton Dickinson Immunocytometry Systems, 1-12 (1998).

Zhou, L. et al., A Distinct Pattern of Cytokine Gene Expression by Human CD83.sup.+ Blood Dendritic Cells, Blood, 86 (9) : 3295-3301 (1995).

Zoeteweij, J.P. et al., HIV-Dendritic Cell Interactions Promote Efficient Viral Infection of T Cells, J. Biomed. Sci., 5:253-259 (1998).

D. Becker et al., "Flow-cytometric screening for the modulation of receptor-mediated endocytois in human dendritic cells: implications for the development of an in vitro technique for predictive testing of contact sensitizers", Journal of Immunological Methods, vol. 203, No. 2, pp. 171-180 (Apr. 25, 1997).

* cited by examiner

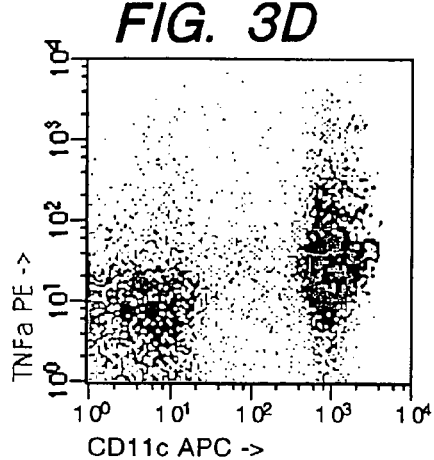
FIG. 3D
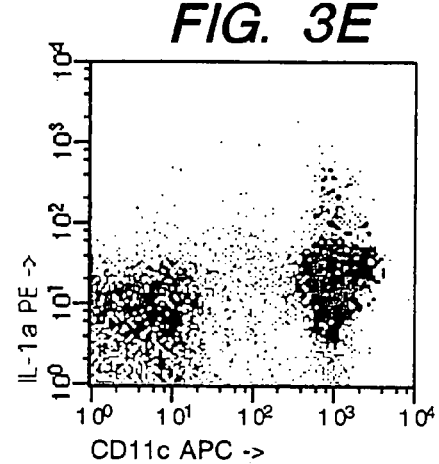
FIG. 3E
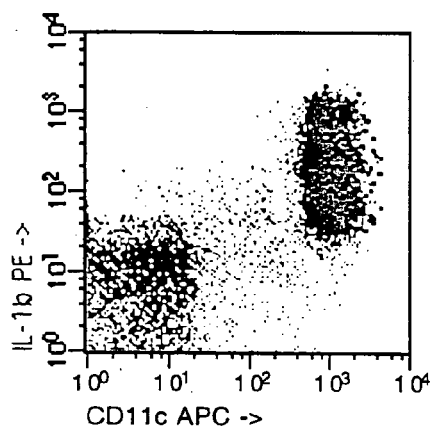
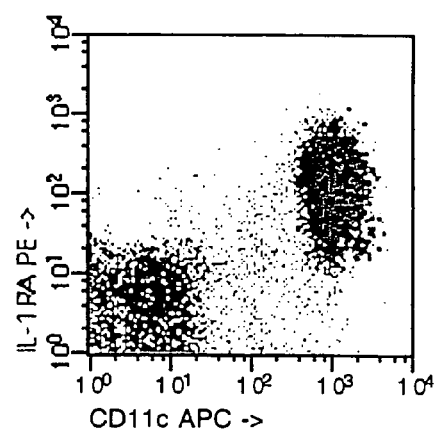
FIG. 3F
FIG. 3G
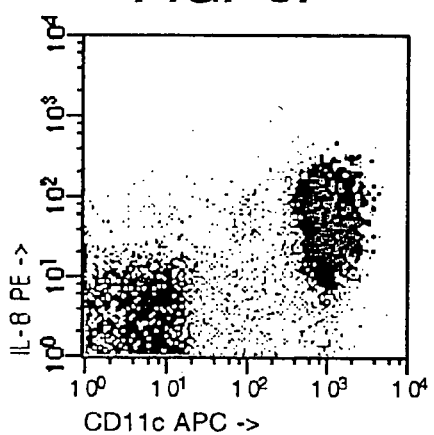
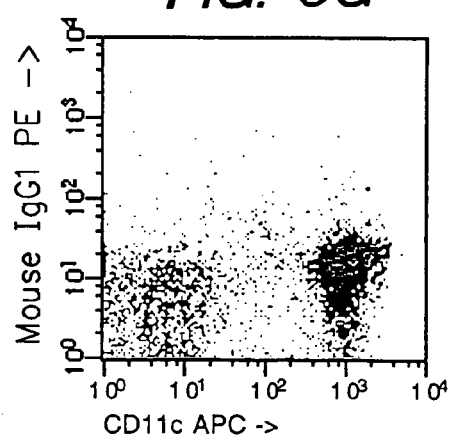
FIG. 3H
FIG. 3I MFI = mean fluorescence intensity
stim = sample containing stimulus
Control = sample kept at 37°C lacking stimulus

FLOW CYTOMETRIC, WHOLE BLOOD DENDRITIC CELL IMMUNE FUNCTION ASSAY

CROSS-REFERENCE TO RELATED APPLICATIONS

This application is a continuation of U.S. Ser. No. 09/787,092, filed Mar. 12, 2001, now abandoned, which is a 371 National Stage application of PCT/US99/21731, filed Sep. 21, 1999, and which is a continuation-in-part of U.S. Ser. No. 09/158,406, filed Sep. 22, 1998, which issued as U.S. Pat. No. 6,495,333, the disclosures of which are incorporated herein by reference in their entirety.

FIELD OF THE INVENTION

This invention relates to assays of blood cell function, and in particular to assays of dendritic cell function in whole blood.

BACKGROUND OF THE INVENTION

Dendritic cells (DCs), first identified a quarter century ago by a characteristic "dendritic" morphology observable in peripheral lymphoid tissues, Steinman et al., *J. Exp. Med.* 137:1142-1162 (1973), are now known to be a morphologically-diverse and widely-distributed cell population. Today, these diverse cells are collectively distinguished by a common function: dendritic cells are the most potent antigen-presenting cells (APCs) of the mammalian immune system, and alone among the various antigen-presenting cells appear capable of triggering a primary T lymphocyte response.

This singular ability to prime a T cell-mediated immune response—combined with a potent ability to present antigen to activated T cells—has implicated dendritic cells as potential reagents for immune-based therapies, as well as likely targets for therapeutic intervention in the treatment of various immune-mediated disorders.

For example, WO 97/24438 describes compositions and methods for co-culturing dendritic cells with T lymphocytes and protein antigen in vitro, thus driving the ex vivo antigen-specific activation of T cells. The activated T cells are then administered autologously to effect an antigen-specific immune response in vivo. Similarly, WO 97/29183 describes a method of activating T cells in vitro by contacting the T lymphocytes with DC that directly express an antigenic protein from a recombinant construct. Again, the activated T cells are intended for autologous infusion. Specific application of DC-driven ex vivo T cell activation to the treatment of prostate cancer is described and claimed in U.S. Pat. No. 5,788,963. In yet another approach, Nemazee, U.S. Pat. No. 5,698,679, describes and claims immunoglobulin fusion proteins that deliver antigenic peptides to targeted antigen presenting cells (APCs), including dendritic cells, in vivo.

Dendritic cells have also been implicated as important in the pathogenesis and pathophysiology of AIDS. One type of DC, the Langerhans cells (LC), is generally believed to be the initial cell type infected with HIV following mucosal exposure to virus. DC are believed to act not only during the initial phase of HIV disease, but also during the chronic phase, facilitating infection and depletion of T lymphocytes. Zoeteweij et al., *J Biomed Sci* 5(4):253-259 (1998). DCs in lymphoid mucosa may represent a key reservoir of viral nucleic acid and virions throughout the course of the disease. Grouard et al., *Curr. Opin. Immunol.* 9(4):563-567 (1997); Weissman et al., *Clin. Microbiol. Rev.* 1997 10(2):358-367 (1997). In vitro methods for screening pharmaceutical candidates for agents that abrogate HIV infection of DC are described and claimed in Steinman et al., U.S. Pat. No. 5,627,025.

Yet despite their importance to the normal mammalian immune response and in immunopathology, DCs have been difficult to study, and particularly difficult to study in their native milieu.

The difficulty stems in part from the rarity of dendritic cells. Although widely distributed, DC are sparse, even in lymphoid tissues, and represent no more than about 0.3%-0.5% of nucleated cells in human peripheral blood.

A further difficulty arises from the absence of DC-specific cell surface markers that would readily permit the positive immunoselection of DCs from mixed populations of cells.

Extensive efforts to identify surface markers that define DCs have been only partially successful. As a result, DCs are presently identified by multiple-marker panels, with identification based primarily on the absence of staining with markers for other lineages (i.e., as lin$^-$ cells). The result is that typical DC immunopurification protocols require at least one immunodepletion step, eliminating cells of various nondendritic blood lineages—lymphocyte, monocyte, granulocyte, and NK lineages, e.g.—coupled with at least one immunoenrichment step. The immunoenrichment step may, for example, include selection for CD4$^+$ cells (Blood Dendritic Cell Isolation Kit, Miltenyi Biotec #468-01, Auburn, Calif.), or, in the alternative or in addition, selection for HLA-DR expression, Ghanekar et al., *J. Immunol.* 157: 4028-4036 (1996).

These serial manipulations, however, may substantially alter the DC cell phenotype from that present in vivo. For example, lin$^-$HLA-DR$^+$CD123$^+$ dendritic cells in fresh preparations of tonsillar mononuclear cells express low levels of the T cell costimulatory molecules CD80 (B7.1), CD86 (B7.2), and HLA-DQ. Even an overnight culture of these cells in the absence of added cytokines is sufficient to induce the mature DC phenotype with upregulation of CD86, CD80, HLA-DQ and HLA-DR. Olweus et al., *Proc. Natl. Acad. Sci. USA* 94(23): 12551-12556 (1997). Longer term culture of CD34$^+$ dendritic cell precursors in the presence of cytokines effects substantial phenotypic changes. Caux et al., J. Exp. Med. 184:695, 1996; Olweus et al., *Proc. Natl. Acad. Sci. USA* 94(23):12551-12556 (1997).

Thus, there exists a need in the art for methods of assaying dendritic cells without prior immunopurification or in vitro culture.

The paucity of DC-specific cell surface markers further suggests that surface immunophenotypic markers may only incompletely distinguish dendritic cell subsets that are, nonetheless, functionally distinct. For example, peripheral blood dendritic cells have been shown to fall into two subsets distinguishable by the divergent expression of CD11c and CD123: one subset is CD11c$^+$CD123$^{low}$, the other CD11c$^-$CD123$^+$. Olweus et al., *Proc. Natl. Acad. Sci. USA* 94(23): 12551-12556 (1997). Yet the critical and disparate roles that dendritic cells play in the immune system would argue that these two subsets each likely encompasses a variety of cell types with disparate functional activity.

There thus exists a need in the art for methods of distinguishing dendritic cell subsets using phenotypic criteria other than, or in addition to, expression of cell-surface markers. There further exists a need for methods of subsetting DC based on criteria that may be related more directly to DC function.

Recently, several groups have reported that intracellular staining of cells using cytokine-specific antibodies permits the flow cytometric analysis of cytokine expression in highly purified blood cell lineages, including purified dendritic cells. Picker et al., *Blood* 86(4):1408-1419 (1995); Waldrop et al., *J. Clin. Invest.* 99:1739-1750 (1997); Ghanekar et al., *J. Immunol.* 157:4028-4036 (1996); de Saint-Vis et al., *J. Immunol.* 160:1666-1676 (1998). More recently, Suni et al., *J. Immunol.* 212:89-98 (1998) described an assay for concurrent expression of intracellular cytokines and cell surface proteins in antigen-stimulated T lymphocytes without prior T cell purification. Similar assays are described and claimed in co-owned and copending U.S. patent application Ser. Nos. 08/760,447 and 08/803,702.

There exists a need in the art for a method that would adapt intracellular cytokine assays to the measurement of cytokine production by unpurified DC cells in whole blood.

SUMMARY OF THE INVENTION

The present invention solves these and other problems in the art by providing, in a first aspect, a flow cytometric method for measuring dendritic cell function in whole blood, comprising the steps of: (a) contacting a whole blood sample with a dendritic cell activator; (b) contacting the sample with a plurality of dendritic cell-distinguishing antibodies and at least one cytokine-specific antibody; and then (c) flow cytometrically assaying the sample for the binding of cytokine-specific antibody by at least one distinguishable DC subset.

In preferred embodiments, activation is performed in the presence of an inhibitor of protein secretion, and following permeabilization of the cells cytokines are detected intracellularly. Thus, in a particularly preferred embodiment, the dendritic cell activator contacting step is performed in the presence of Brefeldin A, and the antibody contacting step itself comprises the steps, in order, of: (b1) adding a plurality of dendritic cell-distinguishing antibodies to the sample; (b2) lysing erythrocytes in the sample; (b3) permeabilizing nucleated cells in the sample; and then (b4) adding at least one cytokine-specific antibody to the sample.

The dendritic cell-distinguishing antibodies may include a plurality of non-DC lineage-specific antibodies. In such cases, it is particularly preferred that each of the non-DC lineage-specific antibodies be conjugated to the identical fluorophore. When a plurality of non-DC lineage-specific antibodies is used, the dendritic cell-distinguishing antibodies further include an antibody specific for HLA-DR.

In a preferred embodiment, subsets of dendritic cells are distinguishably labeled. In this embodiment, the dendritic cell-distinguishing antibodies include at least one antibody that binds differentially to the surface of the different dendritic cell subsets. Particularly preferred in this embodiment is the use of antibody specific for CD11c or CD123.

The function of DCs can be characterized by their cytokine expression patterns and by the dynamic regulation of differentiation/activation markers (CMRF-44, CMRF-56, CD83, CD25), of co-stimulatory molecules (CD40, CD80, CD86) and of class II major histocompatibility complexes (MHC class II). Thus, in a second aspect, the invention provides a flow cytometric method for measuring dendritic cell function in whole blood, comprising: (a) contacting a whole blood sample with a dendritic cell activator; (b) adding to the sample a plurality of dendritic cell-distinguishing antibodies and at least one antibody specific for a dendritic cell surface marker indicative of dendritic cell activation; and then (c) flow cytometrically assaying said sample for the binding of said antibody specific for the dendritic cell surface activation marker by at least one distinguishable DC subset. The dendritic cell surface activation marker is usefully selected from the group consisting of differentiation/activation markers (CMRF-44, CMRF-56, CD83, CD25), of co-stimulatory molecules (CD40, CD80, CD86) and of class II major histocompatibility complexes (MHC class II).

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIGS. 3A-3I presents a series of dot plots generated during the flow cytometric analysis of whole blood activated with PMA+I in the presence of Brefeldin A, as described in example 3;

FIGS. 4A-4K presents a series of dot plots generated during the flow cytometric analysis of whole blood incubated in the presence of brefeldin A to the absence of activator (resting control), as described in example 3;

DETAILED DESCRIPTION OF THE INVENTION

Figure 1:
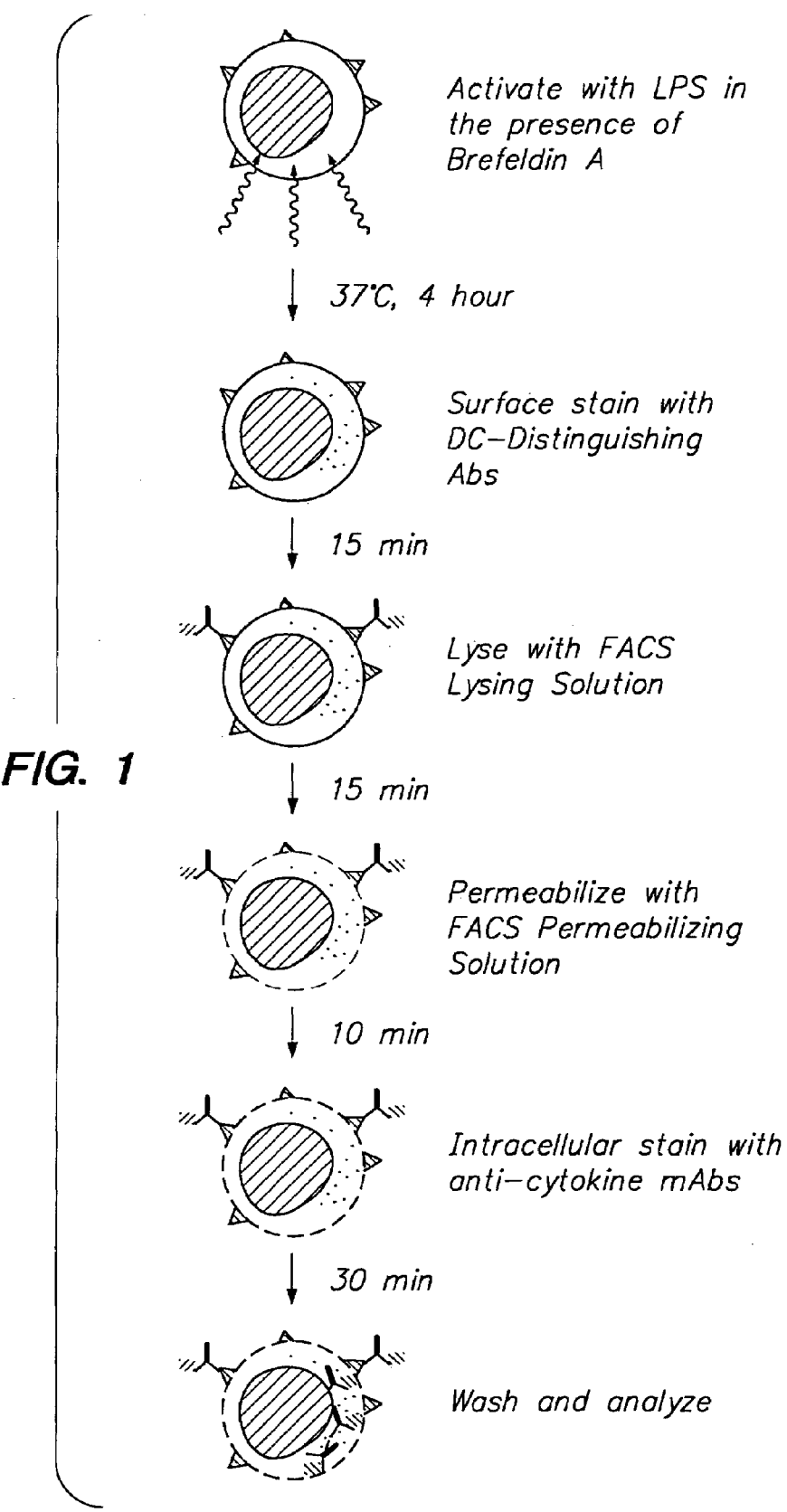
FIG. 1 is a flow chart schematizing the basic steps in a whole blood flow cytometric assay for dendritic cell function, with LPS exemplified as the dendritic cell activator.

In order that the invention herein described may be fully understood, the following detailed description is set forth. In the description, the following terms are employed:

By "whole blood" is intended a fluid blood sample as drawn from a mammal and substantially unfractionated thereafter. That is, if fractionation is performed subsequent to blood draw, the fractionation has raised the percentage of dendritic cells to no more than about 5%, preferably no more than about 1-4%, most preferably no more than 1%, of total nucleated cells;

"Antibody" includes all products, derived or derivable from antibodies or from antibody genes, that are useful as markers in the flow cytometric methods described herein. "Antibody" thus includes, inter alia, natural antibodies, antibody fragments, antibody derivatives, and genetically-engineered antibodies, antibody fragments, and antibody derivatives;

"Dendritic cell-distinguishing antibody" includes any antibody that may be used, alone or in combination with other antibodies, to facilitate identification of dendritic cells, and thus includes antibodies that are specific for epitopes displayed by non-DC lineages and further includes antibodies that bind to structures displayed by DC that prove useful for positive immuno-identification;

"Lineage negative", also abbreviated "lin$^-$", denominates the absence of cell surface markers known to be characteristic of non-dendritic lymphopoietic or hematopoietic cell lineages. By "absence" is intended a level of surface expression, as measured in an immunoassay, such as a flow cytometric assay, that is not significantly different from background;

A "dendritic cell activator" is any substance that is capable of inducing or upregulating expression of cytokines, chemokines, or detectable cell surface proteins by dendritic cells;

All remaining terms have their usual meaning in the flow cytometric arts, as set forth, inter alia, in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); and *Practical Flow Cytometry*, 3rd ed., Wiley-Liss (1995).

Dendritic cells (DC) capture, process and present antigen to naive and memory T cells, and thus play a pivotal role in the mammalian immune response. An understanding of DC function is critical to any detailed understanding of mammalian immune function. Yet functional studies of dendritic cells have in the past been hampered by the functional diversity of the cells that are collectively so denominated.

For example, studies of peripheral blood dendritic cells were for two decades conducted without awareness of the fact that peripheral blood dendritic cells fall into two mutually-exclusive subsets distinguishable by cell surface immunophenotype. Thomas et al., *J. Immunol.* 153:4016 (1994); O'Doherty et al., *Immunology* 82:487-493 (1994); Olweus et al., *Proc. Natl. Acad. Sci. USA* 94(23): 12551-12556 (1997). Both subsets express high levels of HLA-DR and lack markers characteristic of other lineages (CD3, CD14, CD19, CD20, CD16, CD56). The subsets are distinguished from one another by their divergent expression of CD11c and CD123: one subset is CD11c$^+$CD123$^{low}$, the other CD11c$^-$CD123$^+$. O'Doherty et al., *Immunology* 82:487-493 (1994); Olweus et al., *Proc. Natl. Acad. Sci. USA* 94(23): 12551-12556 (1997); Willmann et al., "Peripheral Blood Dendritic Cells Revealed by Flow Cytometry" (Becton-Dickinson Application Note 3) (1998).

The two peripheral blood DC subsets that were first identified by fortuitous cell surface distinctions have now been shown to be functionally distinct. It is known, for example, that the CD11c$^+$CD123$^{low}$ DC subset proves more potent than the CD11c$^-$CD123$^+$ subset in stimulating T cells in a mixed lymphocyte reaction (MLR). And as shown newly herein, the CD11c$^+$ subset alone responds to DC activators with upregulation of cytokine production and increased surface expression of T cell costimulatory molecules.

The two decades that intervene between the first identification of DC and the first demonstration that peripheral blood contains immunophenotypically and functionally discrete DC subsets speak to the insufficiency of surface phenotyping fully to capture the functional diversity of dendritic cells.

The present invention permits peripheral blood dendritic cells to be described and distinguished based upon differences in their functional responses to DC activators. The invention further permits these functional responses to be measured with minimal experimental intervention, precluding the known phenotypic plasticity of dendritic cells from confounding the results.

FIG. 1 schematizes the basic method of the present invention. A sample of whole blood is first incubated with a DC activator. LPS is exemplified in the figure.

Incubation with the dendritic cell activator serves to drive the differential phenotypic response of the various DC subsets present in the sample; measurement of these differences permits the discrimination of DC subsets that might otherwise prove indistinguishable. Different activators produce different sets of responses, permitting still finer distinctions to be drawn. Although both FIG. 1 and the experiments reported herein exemplify the invention using DC activators with broad and pleiotropic effects, such as LPS, activators with finer specificity will also prove useful.

Incubation with a dendritic cell activator is particularly shown differentially to upregulate the production of various cytokines by peripheral blood dendritic cells which, absent stimulation, produce no detectable cytokines. By performing the activation step in the presence of Brefeldin A ("BFA"), which disassembles the Golgi complex (Openshaw et al., *J. Exp. Med.* 182:1357 (1995); Chardin and McCormick, *Cell* 97:153 (1999)), inhibiting protein transport through the cellular secretion pathway, cytokine proteins accumulate in the cells and may be detected flow cytometrically in a later step of the assay. Similar results would be obtained using equivalent inhibitors of secretion, such as monensin.

After incubation in the presence of activator and BFA, the surface of the cells is stained with fluorophore-conjugated antibodies.

This surface staining step includes, as a first class of antibodies, a plurality of dendritic cell-distinguishing antibodies. A dendritic cell-distinguishing antibody is any antibody that may be used, alone or in combination with other antibodies, to facilitate identification of dendritic cells. Thus, the antibodies used in this step may include (1) antibodies that preferentially bind non-dendritic cells, and (2) antibodies that bind to dendritic cell surface structures useful in identifying DC.

As to the first such category, a cocktail of lineage-specific antibodies labeled with the identical fluorophore may advantageously be used. One such cocktail available commercially is the lin 1 FITC lineage cocktail from Becton Dickinson Immunocytometry Systems (BDIS, San Jose, Calif., catalogue number 340546), which contains a mixture of antibodies specific for CD3, CD14, CD16, CD19, CD20, and CD56, each conjugated to fluorescein isothiocyanate (FITC). In combination, the antibodies in the cocktail stain lymphocytes, monocytes, eosinophils, and neutrophils, but not dendritic cells. The DC in the labeled sample thus assort into the FITC$^-$ or FITC$^{low}$ class. The lin 1 cocktail is particularly advantageous in that the concentration of antibodies and degree of conjugation have been titrated to provide equivalent intensity fluorescence signals from the cells of the various non-DC lineages that are bound by the antibodies.

As to the second category of dendritic cell-distinguishing antibodies there is, as yet, no cell surface marker that alone positively identifies dendritic cells. When such DC-specific surface structure is identified, an antibody thereto may be used alone in this stage of the protocol. At present, however, the use of antibodies in the second category of DC-distinguishing antibodies—antibodies that affirmatively bind to dendritic cell surface structures—obligates the additional use of DC-distinguishing antibodies from the first category, i.e., those that identify non-dendritic lineages.

Conversely, antibodies from the first category of DC-distinguishing antibodies—those that preferentially bind non-dendritic cells—cannot at present be used without at least one antibody from the second category. Basophils are lin$^-$CD123$^{high}$CD11c$^+$ but HLA-DR$^-$; when antibodies that preferentially bind non-dendritic cells (category 1) are used in the assay, an anti-HLA-DR antibody must also be used.

If dendritic cell-distinguishing antibodies of both first and second category are used, the antibodies in the two categories are preferentially labeled with fluorophores that are flow cytometrically distinguishable.

The surface staining step may optionally also include, as a second broad class, antibodies that distinguish known dendritic cell subsets. Thus, antibodies specific for CD11c or CD123 prove particularly useful, as these antigens are known to define mutually exclusive peripheral blood DC subsets. The fluorophore used should be flow cytometrically distinguishable. Thus, where antibodies used later in the assay for intracellular staining are labeled with phycoerythrin (PE), a typical surface staining scheme would include, e.g., lin 1 FITC, HLA-DR PerCP, and CD11c APC (in this nomenclature, the antibody is identified by its specificity, followed by the fluorophore).

After surface staining, the red cells in the sample are lysed and the nucleated cells then permeabilized. These two steps may be accomplished using commercially available reagents, such as FACS® Permeabilizing Solution and FACS® Lysing solution (BDIS catalogue numbers 340457 and 349202, respectively), according to the manufacturer's instructions.

Following permeabilization, the cells are stained intracellularly using fluorophore-conjugated antibodies that are specific for cytokines. The fluorophore conjugated to the cytokine-specific antibodies is preferentially distinguishable in a flow cytometric assay from any of those used for surface staining.

After intracellular staining, the cells are washed and then analyzed using a flow cytometer, preferably one capable of simultaneous excitation and detection of multiple fluorophores.

FIG. 1 does not schematize the assay for detecting changes in the surface expression of dendritic cell activation markers, which differs in some respects from that used to detect changes in cytokine expression.

In such an assay, activation of dendritic cells in whole blood is performed in the absence of secretion inhibitor, such as Brefeldin A. This precludes the concurrent measurement, in any such sample, of intracellular cytokine expression.

After incubation in the presence of activator, the surface of the cells is stained with fluorophore-conjugated antibodies. In this step, a plurality of dendritic-cell distinguishing antibodies is used, optionally with antibodies that distinguish known dendritic cell subsets, as above-described.

In addition, however, a third class of surface-staining antibodies is used. These are antibodies that recognize surface structures, typically proteins, the expression of which is altered by the prior incubation with dendritic cell activator. For example, activation of peripheral blood dendritic cells is known to cause upregulation of the T cell costimulatory molecules CD80 (B7.1), CD86 (B7.2) and HLA-DQ. Olweus et al., *Proc. Natl. Acad. Sci. USA* 94:12551-12556 (1997). Thus, the surface staining step, as desired, may include antibodies specific for one or more of these antigens. Recent reports identify CD83 and CMRF-44 as cell surface markers that are expressed at high levels on activated or cultured DCs from blood and lymphoid tissue; antibodies specific for these markers may also advantageously be used. Antibodies of this class, if used, are typically conjugated to a fluorophore that is flow cytometrically distinguishable from the antibodies described above. Thus, a typical surface staining scheme would include, e.g., lin 1 FITC, HLA-DR PerCP, CD11c APC, and an antibody specific to a DC surface activation antigen labeled with PE.

After surface staining, the red cells in the sample are lysed and the cells are washed and then analyzed using a flow cytometer, preferably one capable of simultaneous excitation and detection of multiple fluorophores.

As further elaborated in the experimental examples hereinbelow and FIGS. 2-8, whole blood samples from normal volunteers were assayed for dendritic cell function. Preparations were activated with either lipopolysaccharide ("LPS"), phorbol 12-myristate 13 acetate ("PMA") plus ionomycin ("I") (together, "PMA+I") or CD40-crosslinking, each for 4 hours at 37° C. Substances attempted as activators that elicited no cytokine production—PHA, CD2/2R (BDIS Cat. No. 340366), SEB (staph enterotoxin B), CMV, and crosslinking of CD49d —are not reported. CD40 crosslinking effected changes in surface antigen expression but failed to elicit cytokine production.

Table 1 lists the cytokines that were assayed in one or more of the experiments, further classified according to the DC activator used in the experiment. A plus ("+") indicates that expression of the respective cytokine was assessed in one or more experiments; a minus ("−") indicates that expression of the respective cytokine was not assessed. Table 1 does not report the level of expression, which follows in Table 2.

TABLE 1

| Cytokines Assayed | | | |
|---|---|---|---|
| | LPS | PMA + I | CD40 crosslinking |
| IL-1α | + | + | + |
| IL-1β | + | + | + |
| IL-1RA | + | + | + |
| IL-2 | + | + | − |
| IL-4 | + | + | − |
| IL-6 | + | + | + |
| IL-8 | + | + | + |
| IL-10 | + | + | + |
| IL-12 | + | + | + |
| IL-13 | + | + | + |
| TNFα | + | + | + |
| IFN-γ | + | − | − |

Table 2 presents the functional responses of the CD11c+ and CD11c− dendritic cell subsets, stimulated with either LPS or PMA+I, and assayed in whole blood. Cytokine expression is measured as mean fluorescence intensity (MFI); the change in surface molecule expression is measured as a ratio of mean fluorescence intensities (MFI) of activated versus control sample.

TABLE 2

DC Functional Responses

| | LPS CD11c+ | PMA + I CD11c+ | LPS CD11c− | PMA + I CD11c− |
|---|---|---|---|---|
| IL-1α | − | −/+ | − | − |
| IL-1β | + | + | − | − |
| IL-1RA | + | + | − | − |
| IL-2 | − | − | − | − |
| IL-4 | − | − | − | − |
| IL-6 | + | − | − | − |
| IL-8 | + | + | − | − |
| IL-10 | − | − | − | − |
| IL-12 | −/+ | − | − | − |
| IL-13 | − | − | − | − |
| TNFα | + | + | − | − |
| IFN-γ | − | N.A. | − | N.A. |
| CD25 | + | −/+ | + | + |
| CD40 | + | + | + | −/+ |
| CD80 | + | + | −/+ | − |
| CD86 | + | + | −/+ | − |
| HLA-DQ | + | + | − | −/+ |
| HLA-DR | + | + | − | −/+ |

The results of these experiments, quite surprisingly, demonstrated the CD11c−CD123+ subset failed to produce any of the tested cytokines, no matter which DC activator was used. When assayed for changes in surface antigen expression, this subset demonstrated clear upregulation of CD25 expression upon PMA+I activation; upregulation of CD25 was the only distinct response observed in CD11c−CD123+ DCs for all investigated stimuli.

In striking contrast, the CD11c+CD123$^{low}$ DCs showed easily measured changes in cytokine expression when stimulated with LPS or PMA+I.

Figure 7A:
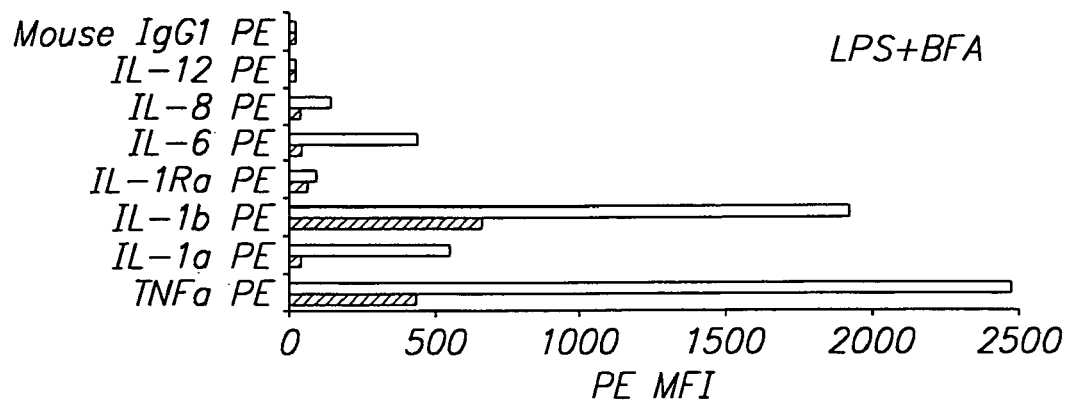
FIG. 7A-B shows a comparison of cytokine expression between monocytes (gray bars) and CD11c$^+$ DCs (black bars) in activated whole blood, with FIG. 7A showing LPS+Brefeldin A-stimulated cells, and FIG. 7B showing PMA+I+Brefeldin A-stimulated cells.
Figure 7B:
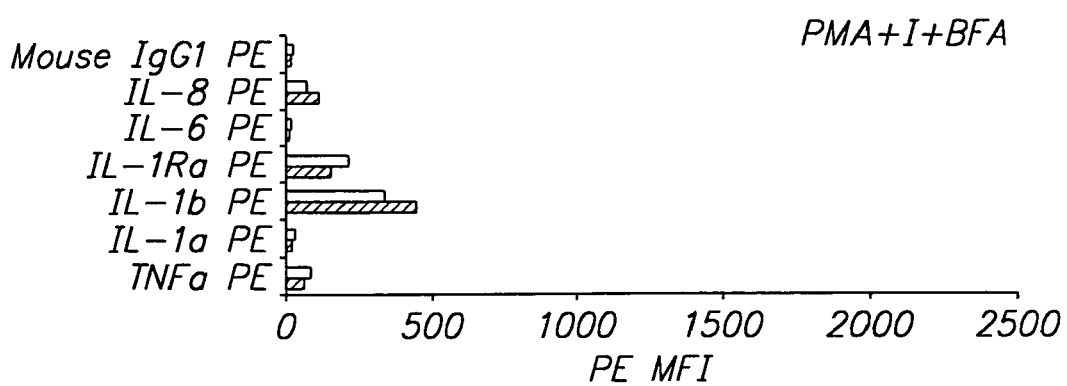

With LPS stimulation, CD11c+ cells produced high levels of TNFα and IL-1β, lower levels of IL-6, IL-1RA and IL-8, and trace levels of IL-12 and IL-1a. The response to LPS is surprising: the CD11c+CD123$^{low}$ DC are CD14−, and CD14 is the principal LPS receptor. It seems likely that LPS acts additionally through a second receptor, perhaps CD11c− itself. Consistent with that hypothesis, the CD11c− DCs, which lack both CD14 and CD11c, fail to respond to LPS stimulation with increased intracellular cytokine expression. Further consistent with this hypothesis, CD14+CD11c+ monocytes respond to LPS stimulation much more potently than do CD14−CD11c+ DCs (FIG. 7A), without showing significantly increased response to PMA+I (FIG. 7B).

Figure 8:
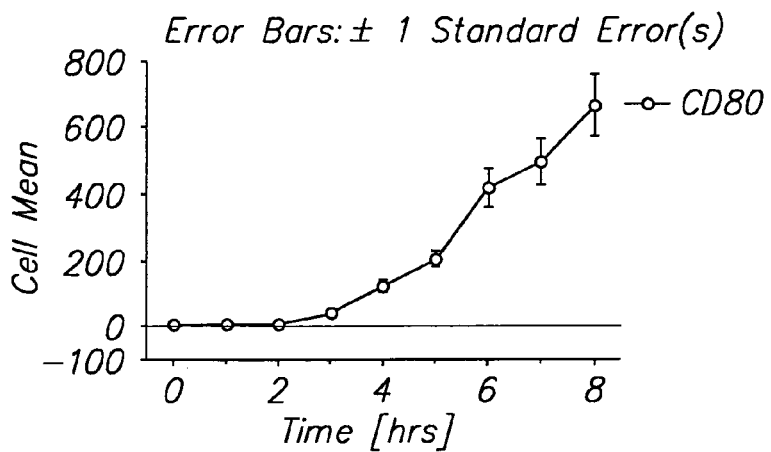
FIG. 8 shows kinetics of TNFa, IL-1β, IL-6 and CD80 in LPS activated CD11c$^+$ DCs. The time course of LPS incubation was 0 to 8 hours. Intracellular cytokine and CD80 expression is measured as PE mean fluorescence intensity (MFI).
Figure 8:
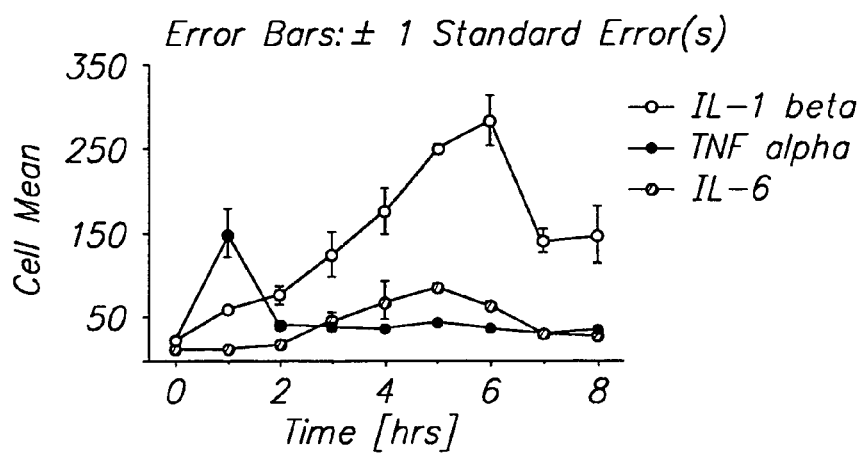

FIG. 8 further shows the kinetics of the response of CD11c+ DCs to LPS. TNFα is produced first, followed by IL-1β and IL-6. CD80 is intensely upregulated after about 4 hours of activation.

With PMA+I activation, CD11c+ cells produced IL-8 and IL-1β, lower but significant levels of IL-1RA and TNFα, trace amounts of IL-1α, and no detectable IL-6.

Thus, differences in the cytokine responses of the CD11c+ DC subset to various activators were readily observed. Principal among these differences is the expression of IL-6 uniquely when stimulated with LPS, and the altered relative expression of IL-8 and TNFα.

The activation of CD11c+ DCs in whole blood also led to an increased expression of accessory molecules. LPS activation triggered upregulation of CD25, CD40, CD80, CD86, HLA-DR and HLA-DQ. The T cell co-stimulatory molecules, in particular CD80, gave the strongest signal. PMA+I led to an upregulation of CD86, CD80, HLA-DQ and HLA-DR. Minimal increase of CD25 and CD40 were observed.

Activation via crosslinking of CD40 resulted in increased levels of CD86, CD80, and minimal upregulation of HLA-DR.

These data, as further detailed in the experimental examples that follow, demonstrate that peripheral blood DC subsets may readily be distinguished in whole blood by their differential production of cytokines and/or cell surface proteins in response to DC activators.

Furthermore, because the dendritic cells that were observed to respond to DC activators fall into a subset (CD11c+) known to be more potent in T cell activation than is the subset (CD11c−) showing no such response, the data further demonstrate that the parameters measured in the method of the present invention—cytokine production and upregulation of surface activation antigens—directly correlate with DC function.

The ease with which the present invention permits measurement of DC function in whole blood, without prior DC purification, was unexpected, because the low frequency of DCs in blood, coupled with the tendency of activated DCs to adhere to equipment, had earlier suggested that too few events could be assayed in a blood sample of clinically-relevant size.

The ability to measure DC function in whole blood, without prior DC purification, offers significant advantages.

From a procedural standpoint, the methods of the present invention eliminate the cell loss attendant upon all DC purification schemes, increasing sensitivity and reducing possible systematic bias. Additionally, the minimal perturbation effected by the methods of the present invention reduces the chance for phenotypic changes resulting from experimental intervention. And as a flow cytometric assay, the methods of the present invention permit DC function to be assessed on a cell-by-cell, rather than bulk, basis, permitting fine discrimination.

From the standpoint of the data made newly available by this invention, the methods of the present invention permit, for the first time, the ready and rapid assessment of DC function in whole blood.

As applied to human patients, the methods of the present invention thus permit the measurement of DC function to be added to the existing roster of immune function assays, and will find utility in clinical situations in which such existing immune function tests are presently used. For example, the methods of the present invention may advantageously be used, alone or in conjunction with flow cytometric quantitation of CD4+ T lymphocyte levels, in the clinical staging of AIDS progression. The methods of the present invention may also be used, alone or in conjunction with existing assays, in the assessment of immune function in congenital, rather than acquired, immunodeficiency syndromes, and in the assessment of immune competence following therapeutic immunosuppression or immunoablation. At the other end of the clinical spectrum, the methods of the present invention will also profitably find use, alone or in conjunction with existing assays, in the clinical assessment of various forms of immune hypersensitivity, allergies, or in the clinical assessment of autoimmune diseases such as multiple sclerosis, rheumatoid arthritis, sarcoidosis, or the like.

By permitting the study of DC function in whole blood, the methods of the present invention also permit the ready evaluation of the effects that agents circulating in the blood may have on DC function. In particular, the assay permits the assessment of the specific effects on DC function of pharmaceutical agents that either intentionally or fortuitously affect DC function.

Thus, as applied to the measurement of DC function in experimental mammals, whether outbred, inbred, or transgenic, the methods of the present invention allow pharmaceutical agents to be tested for their in vivo effects on DC function, permitting the selection of agents that desirably demonstrate immunomodulatory effects, or the selection of agents that specifically lack such effects.

As applied to human subjects, the methods of the present invention permit the ready assessment of the intentional or fortuitous effects on DC function of drugs that circulate in the patient's blood, as a complement to existing immune function assays. For example, the methods of the present invention may be used to assist the monitoring and titration of immunosuppressive agents. The methods prove particularly useful in the monitoring and titration of immunosuppressive agents that abrogate, downmodulate, or otherwise interfere with the function of cytokines, chemokines, or growth factors. Conversely, the methods of the present invention also prove particularly useful in the monitoring of the effects of affirmative cytokine therapy, such as therapies involving the administration of interferons in the treatment of multiple sclerosis, the administration of growth factors after myeloablation, or the like.

The methods of the present invention may also be used to monitor immunomodulatory side effects of agents given to effect unrelated clinical goals.

The methods of the present invention are particularly well suited to the experimental and clinical assessment of therapies involving DC cells themselves. Thus, the methods of the present invention find use in the design, assessment, and monitoring of therapies in which autologous dendritic cells are administered after in vitro manipulation, therapies in which dendritic cells are targeted for ablation, either in vitro, to facilitate transplantation, or in vivo, to effect immunosuppression or induction of tolerance, or therapies in which dendritic cells are targeted to increase global or specific immune function.

It will be understood that the dendritic cells that are found circulating in the peripheral blood at the moment that blood is drawn—those assayed in the methods of the present invention—are drawn from a temporal window in the maturation of one or more cell lineages. That is, for each discrete lineage, the cells circulate preferentially during particular phases in the maturational process. Nothing, however, in the methods of the present invention is limited to particular phases in DC maturation. Thus, the methods may equally be applied to CD34$^+$ committed DC precursors that circulate spontaneously, or to CD34$^+$ DC precursors that are mobilized by pharmacological intervention or the like.

The invention may be better understood by reference to the following examples, which are offered by way of illustration and not by way of limitation.

EXAMPLE 1

Materials

Unless otherwise specified, the following reagents were used in the experiments presented herein. For convenience, antibodies are identified by their specificities and conjugated fluorophore. Fluorophores are phycoerythrin (PE), peridinin chlorophyll protein (PerCP), allophycocyanin (APC), fluorescein isothiocyanate (FITC). Thus, an antibody labeled with phycoerythrin (PE) that is specific for TNFα is denominated "TNFα PE".

Antibodies

The following antibodies were obtained from Becton-Dickinson Immunocytometry Systems (BDIS, San Jose, Calif.): TNFα PE; IL-1α PE; IL-1RA PE; IL-1β PE; IL-2 PE; IL-4 PE; IL-6 PE; IL-8 PE; IL-13 PE; IFN-γ PE; CD11c APC (5 µL/test) (0.125 µg/test); HLA-DR PerCP (10 µL/test) (0.125 µg/test); lin 1 FITC (research lot KW98/07 1.1) (20 µL/test); CD40 PE (unconjugated mAb obtained from DNAX Research Institute, Palo Alto, Calif.; custom conjugated to PE at BDIS, BDIS research conjugate PC#931) (10 µL/test) (0.125 µg/test); CD80 PE (20 µL/test); CD25 PE (20 µL/test); HLA-DQ PE (unconjugated mAb obtained from BDIS; custom-conjugated to PE at BDIS, BDIS research conjugate PC#1284) (0.5 µg/test); IgG2a PE (cat. no. 340459, 25 µg/mL); IgG1 PE (cat. no. 340013, 50 µg/mL). CD83 PE (BDIS research conjugate, PC#1520; 50 µg/mL, used at 20 µL per 300 µL whole blood) is also available commercially from Pharmingen (catalogue number 36935X).

The lin 1 FITC lineage cocktail is also available commercially (BDIS, catalogue number 340546), and contains a titrated mixture of antibodies specific for CD3, CD14, CD16, CD19, CD20, and CD56, all labeled with FITC. In combination, the antibodies stain lymphocytes, monocytes, eosinophils, and neutrophils.

The following antibodies were obtained from PharMingen (San Diego, Calif.): IL-10 PE (IgG2a) (0.1 µg/test); IL-12 PE (IgG1) (0.1 µg/test); CD86 PE (clone IT2.2; Cat #33435X, IgG2b) (10 µL/test).

Lysing and Permeabilizing Agents

FACS® Permeabilizing Solution and FACS® Lysing Solution were obtained as 10× stock solutions from BDIS (catalogue numbers 340457 and 349202, respectively), and were diluted and used in accordance with the package insert.

Dendritic Cell Activators

Chemical activators were obtained from Sigma Chemical Company, St. Louis, Mo. Lipopolysaccharide ("LPS") (Sigma catalogue number L2654) was made 0.5 mg/mL in DMSO and stored at −20° C. Ionomycin ("I")(Catalogue number I-0634), was made 0.5 mg/mL in ethanol and stored at −20° C. Phorbol 12-myristate 13 acetate ("PMA") (Catalogue number P-8139) was made 0.1 mg/mL in DMSO and stored at −20° C.

CD40 crosslinking was performed using polystyrene beads (0.84 µm, Baxter) coated with CD40 antibody (PharMingen, San Diego).

Secretion Inhibitor

Brefeldin A ("BFA") (catalogue number B-7651) was made 5 mg/mL in DMSO, and stored at −20° C.

Wash Buffer

Wash buffer consisted of phosphate-buffered saline ("DPBS") (obtained as a 10× stock solution from GibCo-BRL (Grand Island, N.Y.), then diluted with deionized water to 1×), containing 0.5% fetal calf serum (Sigma, St. Louis, Mo.) (fetal calf serum added after dilution of 10× PBS stock to 1×).

EXAMPLE 2

Protocols for Whole Blood Flow Cytometric Dendritic Cell Immune Function Assay Unless otherwise specified, the following protocols were used in the experiments presented herein.

Dendritic Cell Activation

Venous blood of normal donors was collected in sodium heparin VACUTAINER® tubes. For activation with LPS, the blood was stimulated with 1 µg/mL LPS. For activation with PMA+I, whole blood was first diluted 1:1 with RPMI medium (Biowhittaker, Watersville, Md.). PMA was then added at 5 ng/mL and ionomycin at 1 µg/mL. For activation by CD40 crosslinking, 50 µL CD40-coated polystyrene beads was added to 1 mL whole blood. All samples were incubated for four hours at 37° C. in a humidified incubator with 5% $CO_2$.

For detection of intracellular cytokines, activation, as above, was performed in the presence additionally of Brefeldin A (BFA) at 10 µg/mL. Control (resting) aliquots were incubated with BFA alone.

For detection of changes in surface antigen expression, samples were incubated with DC activator, as above, without the further addition of BFA. Control (resting) aliquots were incubated with neither BFA nor activator.

Immunofluorescence Staining of Intracellular Cytokines

Prior to staining, PMA+I treated blood samples were reduced to half volume by centrifugation and removal of supernatant.

Cell preparation was done at room temperature (RT), and all incubation steps were performed in the dark.

For staining, 1 mL of sample (activated or resting blood control) was added to a cocktail of dendritic cell-distinguishing antibodies (20 µL lineage cocktail 1-FITC, 10 µL HLA-DR PerCP, 5 µL CD11c APC; reagent volumes per 50 µL blood) in a 50 mL polypropylene centrifuge tube. The blood was incubated in the presence of the fluorophore-conjugated antibodies for 15 min. After incubation, 40 mL FACS® Lysing Solution was added and the tube incubated for a further 10 min. The cells were then collected by centrifugation for 10 min at 500×g, and the pellet gently broken off for further processing. Next, 10 mL FACS® Permeabilizing Solution was added and the cells were incubated for 10 min. The permeabilization reaction was stopped by addition of 40 mL of buffer (DPBS 1×, 0.5% fetal calf serum). The permeabilized cells were pelleted for 10 min at 500×g and resuspended in the supernatant remaining in the tube after decanting (approximate volume 500 µL).

An aliquot of 50 µL of the extracellularly-stained, lysed and permeabilized cells (sufficient for one test) was added to a polypropylene staining tube and incubated for 30 min in the presence of the cytokine-specific mAb (see Materials, above). The samples were then washed with buffer, resuspended in 250 µL buffer, and subjected to flow cytometric data acquisition as soon thereafter as possible. If flow cytometric data acquisition was delayed, the samples were kept at 4° C. for up to one hour.

Depending upon yield, a 1 mL sample of whole blood yielded about 7 to 12 tests for cytokine expression determination.

Immunofluorescent Staining of Surface Antigens

Prior to staining, PMA+I treated blood samples were reduced to half volume by centrifugation and removal of supernatant.

Cell preparation was done at room temperature (RT) and all incubation steps were performed in the dark.

For staining, 150 µL of sample (activated or resting blood control) was added to a cocktail of monoclonal antibodies in a staining tube. The cocktail included a plurality of dendritic-cell distinguishing antibodies (20 µL lin 1 FITC cocktail, 10 µL HLA-DR PerCP, 5 µL CD11cAPC; reagent volumes per 100 µL blood) and one of the following PE-conjugated antibodies specific for DC surface activation antigens (20 µL CD25 PE, 0.125 µg CD40 PE, 20 µl CD80 PE, 10 µL CD86 PE, 0.5 µg HLA-DQ PE). Blood and mAbs were incubated for 15 min at RT in the dark.

After incubation, 3 mL of FACS® Lysing Solution was added and the tube incubated for 10 min at RT. The lysed cells were centrifuged for 5 min at 500×g and subsequently washed with 3 mL buffer (DPBS 1×, 0.5% fetal calf serum). The cell pellet was resuspended in 250 µL buffer and immediately acquired on a flow cytometer. If data acquisition was delayed, the cells were maintained at 4° C. for up to one hour.

Flow Cytometric Analysis

The samples as described above were acquired on a FACSCalibur™ dual laser flow cytometer (BDIS, San Jose, Calif.). The instrument was set up using automated FACSComp™ 4.0 software and 4-color Calibrite™ beads (BDIS, San Jose, Calif.). Events were acquired on a FSC threshold. To reduce the size of the listmode data files, the acquisition used a live gate on HLA-DR positive events in a lin 1 FITC/HLA-DR PerCP two-parameter distribution.

EXAMPLE 3

Detection of CD11c⁺ DC Cytokine Response in Whole Blood

Whole blood samples were drawn from healthy volunteers and activated with either LPS or PMA+I, both in the presence of Brefeldin A, according to the procedures described in Examples 1 and 2. The results are shown, respectively, in FIGS. 2 and 3.

Figure 2A:
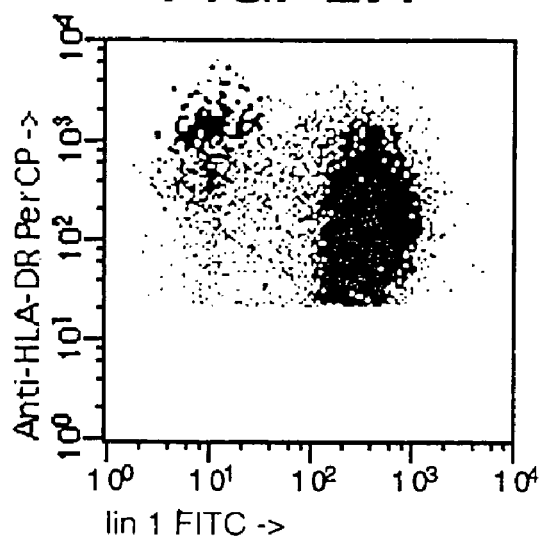
FIGS. 2A-2J presents a series of dot plots generated during the flow cytometric analysis of whole blood activated with LPS in the presence of Brefeldin A, as described in example 3.
Figure 2C:
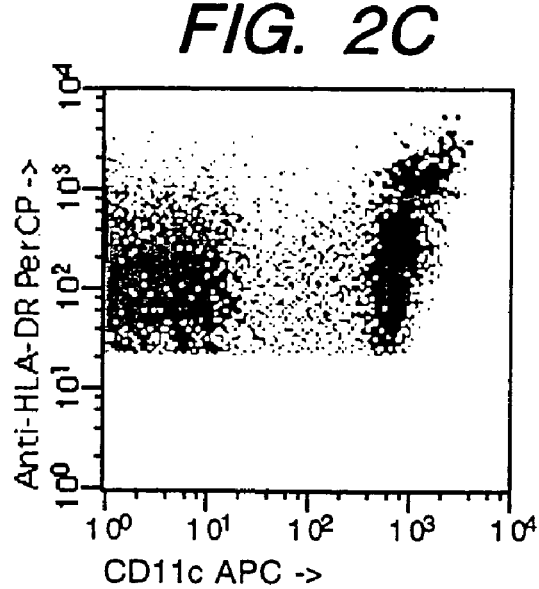
Figure 2B:
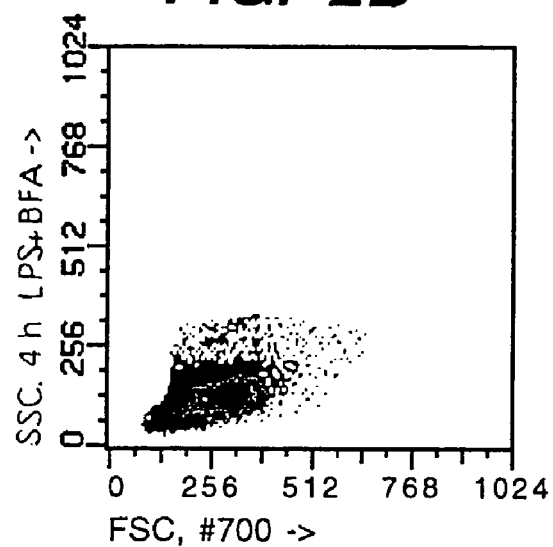
Figure 2D:
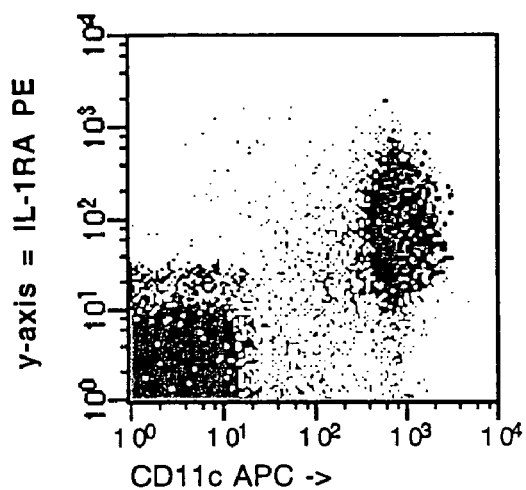
Figure 2E:
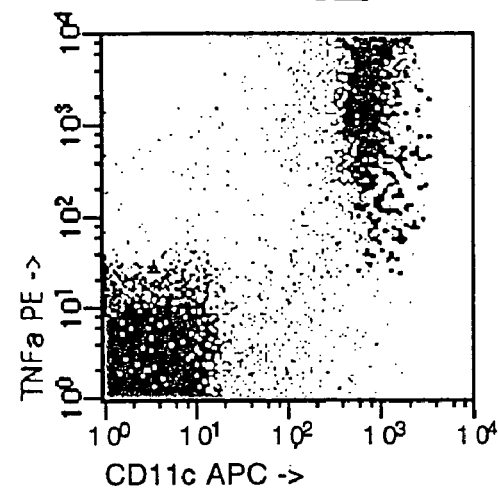
Figure 2F:
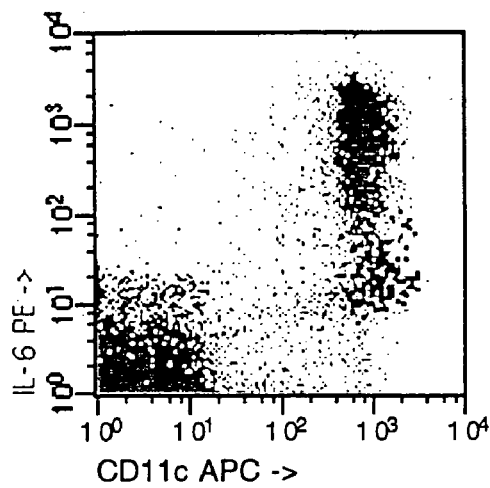
Figure 2G:
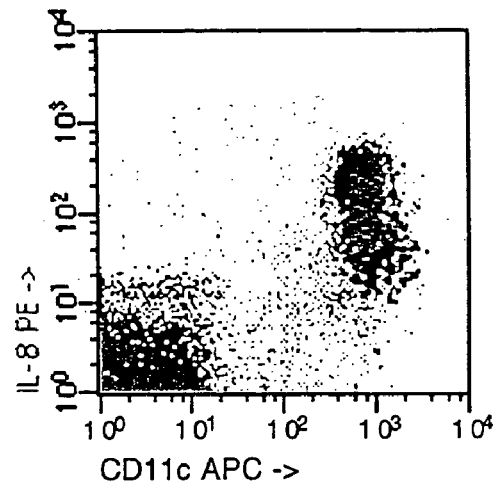
Figure 2H:
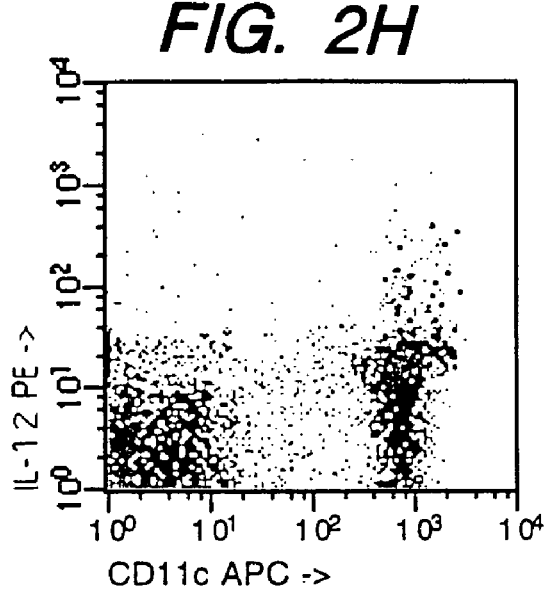

FIGS. 2A-2C show the surface immunophenotypic characteristics of peripheral blood DC from a single LPS-activated whole blood sample. FIG. 2A demonstrates that both dendritic cell subsets are lin 1 $FITC^{dim}$ and $HLA-DR^{bright}$, in agreement with O'Doherty et al., *Immunology* 82: 487-493 (1994); Qlweus et al., *Proc. Natl. Acad. Sci. USA* 94 (23): 12551-12556 (1997), with FIG. 2B further demonstrating that the two subsets have similar side scatter and forward scatter properties. FIG. 2C shows discrimination of the two subsets based on differential levels of CD11c expression.

Figure 2I:
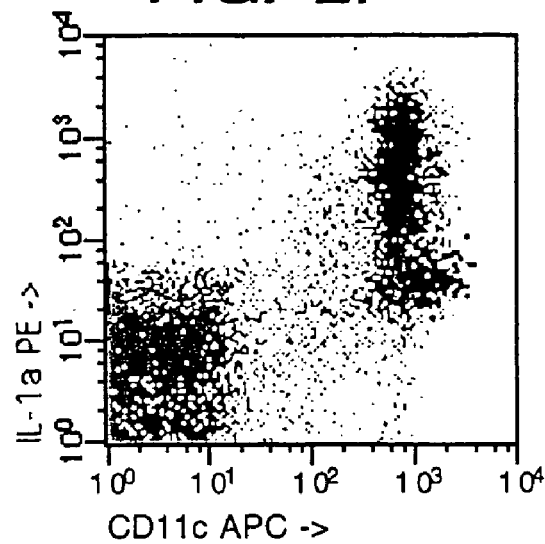
Figure 2J:
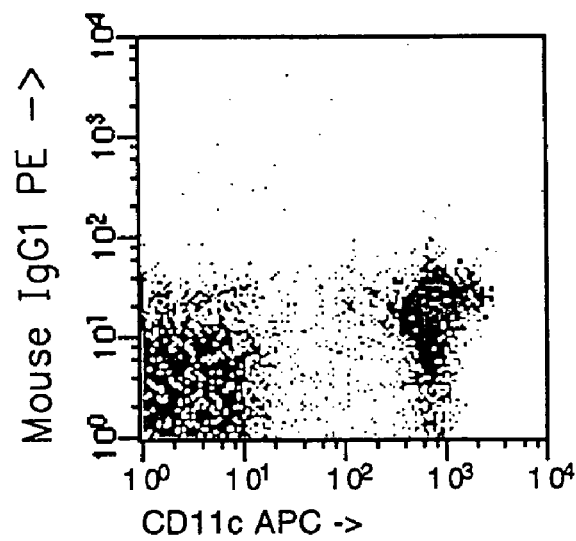

FIGS. 2D-2J show the result of assays for expression of IL-1RA (FIG. 2D), TNFα (FIG. 2E), IL-6 (FIG. 2F), IL-8 (FIG. 2G), IL-12 (FIG. 2H), IL-1α (FIG. 2I). FIG. 2J shows results using an isotype-matched PE-conjugated negative control antibody.

FIGS. 2D-2J demonstrate that the CD11c⁻ (CD123⁺) subset (red) is unresponsive to LPS stimulation, at least as evidenced by the absence of detectable cytokine production. Although not shown directly on these figures, the cytokine levels measured in the LPS-activated CD11c⁻ DC are indistinguishable from those produced in the absence of activator; as shown in FIG. 4, neither CD11c⁻ nor CD11c⁺ subset produces detectable levels of cytokine in the absence of DC activators.

In contrast, the CD11c⁺ population shows much higher levels of cytokine production, with high levels of TNFα and IL-1β, lower levels of IL-6, IL-1RA and IL-8, and trace levels of IL-12 and IL-1a.

Figure 3A:
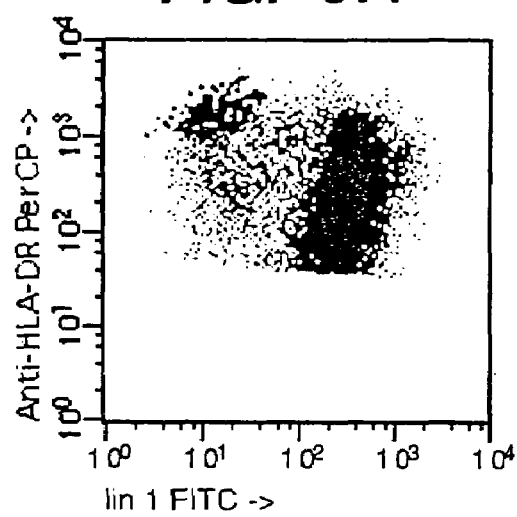
Figure 3C:
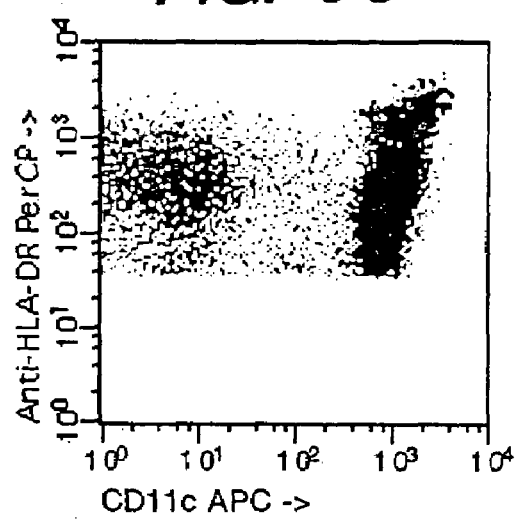
Figure 3B:
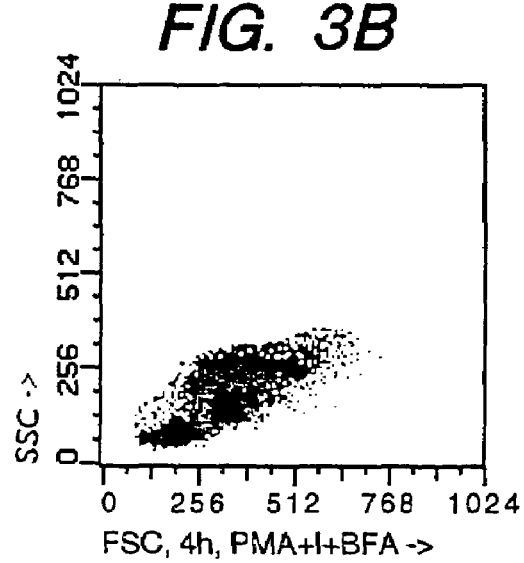
Figure 4C:
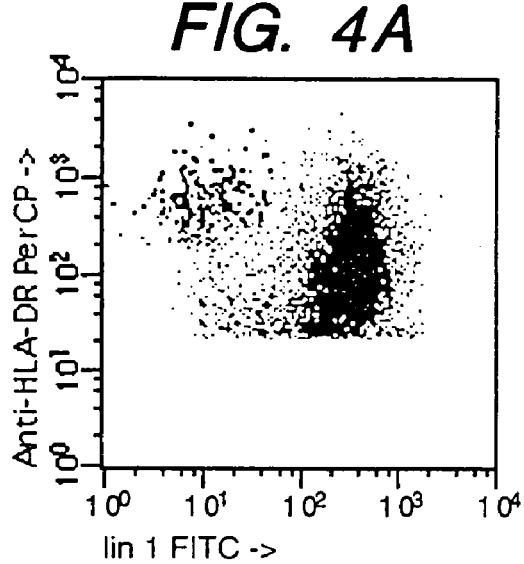
Figure 4C:
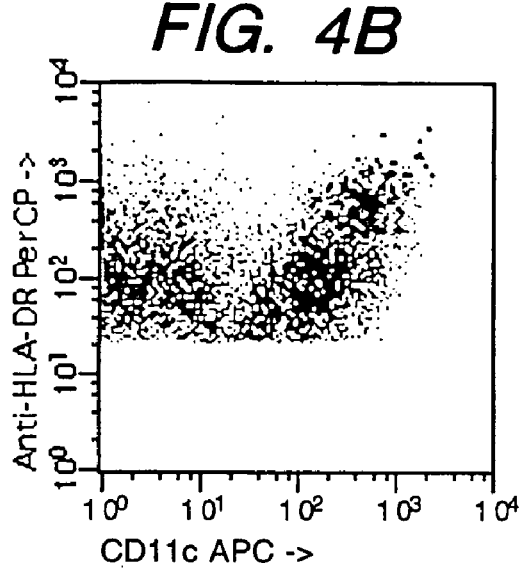
Figure 4C:
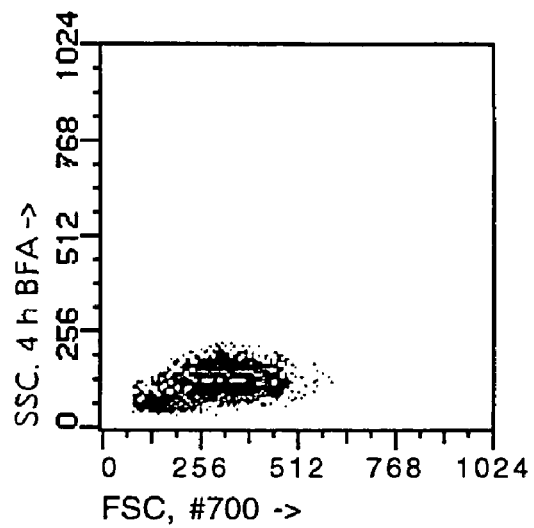
Figure 4D:
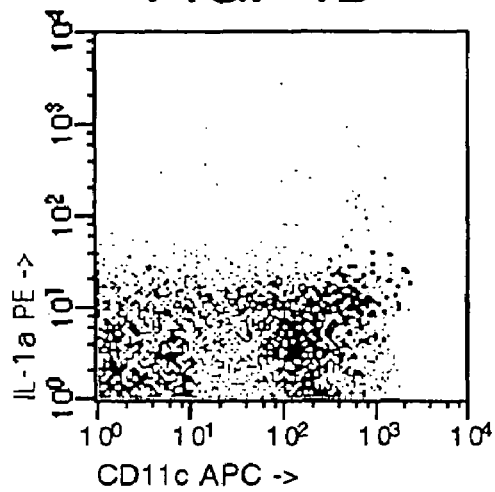
Figure 4E:
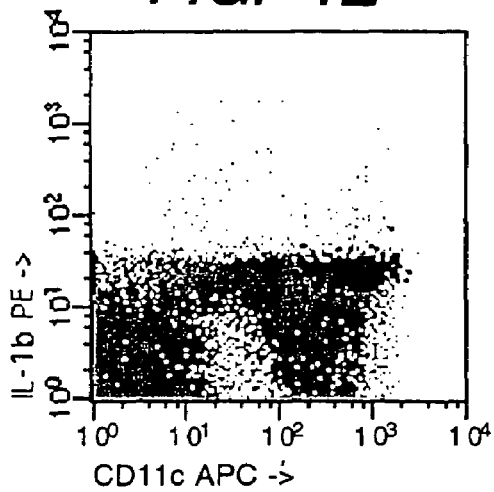
Figure 4F:
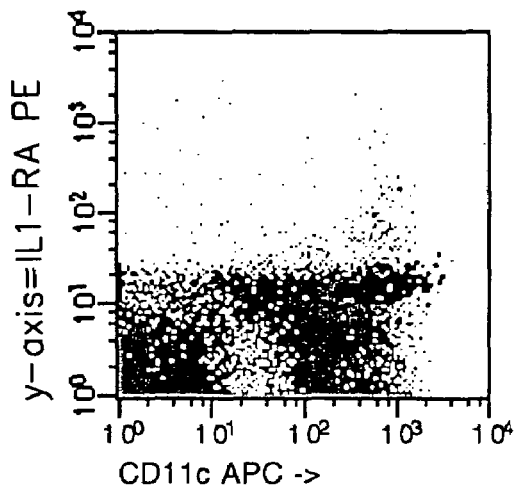
Figure 4G:
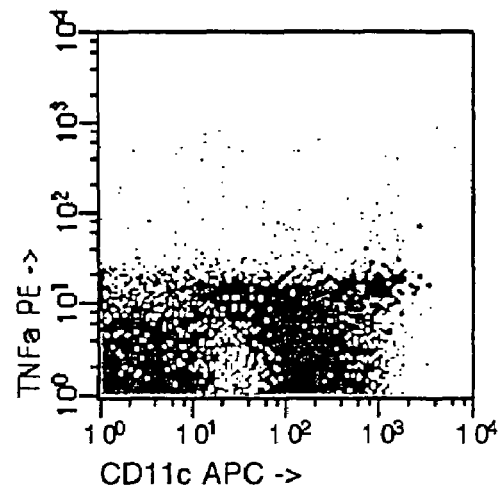
Figure 4H:
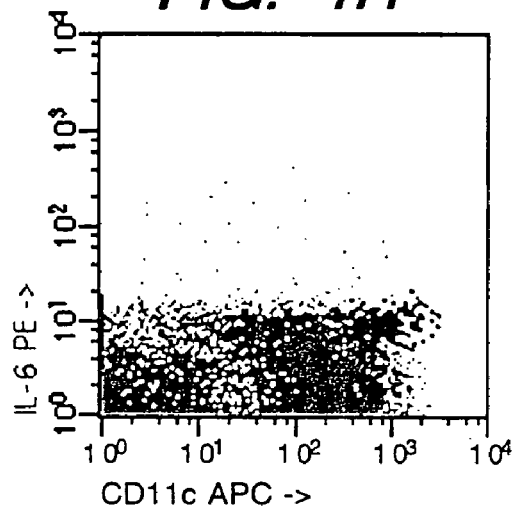
Figure 4I:
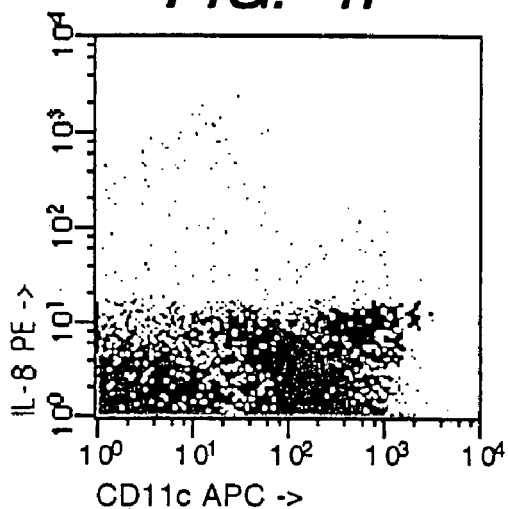
Figure 4J:
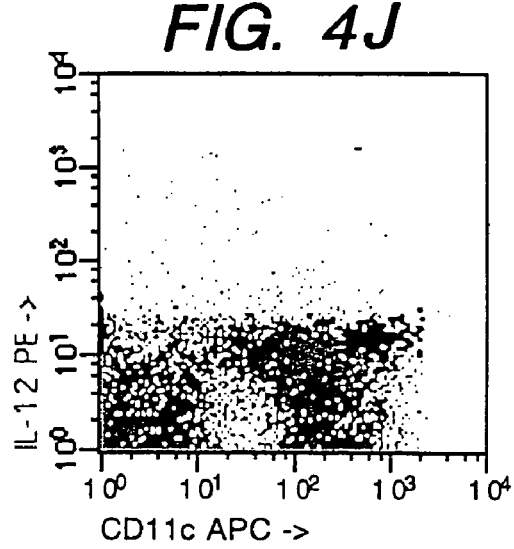
Figure 4K:
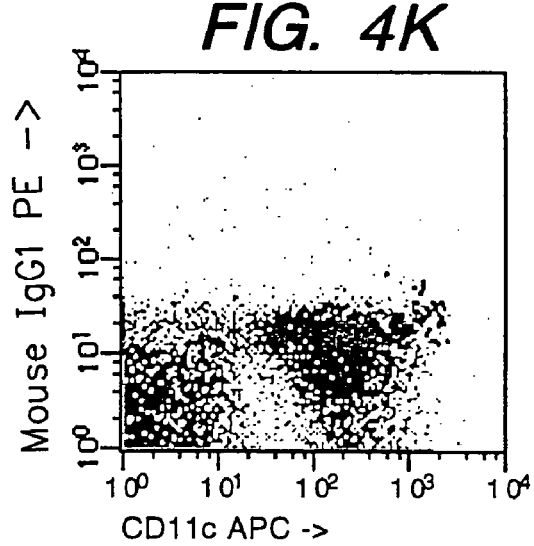

FIGS. 3A-3C show the surface immunophenotypic characteristics of peripheral blood DC from a single whole blood sample activated with PMA+I. CD11c⁺ dendritic cells are painted green, CD11c⁻ DC are painted red, and nondendritic cells appear gray. The colors are arbitrarily chosen for purposes of display, and bear no relationship to the fluorophores used for analysis.

FIG. 3A demonstrates that both dendritic cell subsets are lin 1 FITC$^{dim}$ and HLA-DR$^{bright}$, with FIG. 3B further demonstrating that the two subsets have similar side scatter and forward scatter properties. FIG. 3C shows discrimination of the two subsets based on differential levels of CD11c expression.

FIGS. 3D-3I show the result of assays for expression of TNFα (FIG. 3D), IL-1α (FIG. 3E), IL-1β (FIG. 3F), IL-1RA (FIG. 3G), and IL-8 (FIG. 3H). FIG. 3I shows results using an isotype-matched PE-conjugated negative control antibody.

FIGS. 3D-3I demonstrate that the CD11c⁻ (CD123⁺) subset (red) is unresponsive to PMA+I stimulation, at least as evidenced by the absence of detectable cytokine production. Although not shown directly on these figures, the cytokine levels measured in the LPS-activated CD11c⁻ DC are indistinguishable from those produced in the absence of activator (compare to FIG. 4).

In contrast, the CD11c⁺ population shows much higher levels of cytokine production, with demonstrable production of IL-1β, IL-IRA, TNFα, and IL-8. FIG. 3E demonstrates that CD11c⁺ cells produced trace amounts of IL-1α.

The cytokine expression of monocytes was evaluated in some of the same samples. Monocytes were identified based on their scatter characteristics, their bright lin 1 FITC, anti-HLA-DR PerCP and CD11c APC staining. As can be seen, in LPS+BFA stimulated samples, monocytes express cytokines at higher levels than do CD11c⁺ DCs. Upon PMA+I+BFA activation, the cytokine secretion of CD11c⁺ DCs and monocytes is equivalent, but much less compared to LPS activated samples. Intracellular protein secretion is evaluated as PE mean fluorescence intensity (MFI).

EXAMPLE 4

Detection of CD11c⁺ DC Surface Antigen Expression in Whole Blood

Figure 6A:
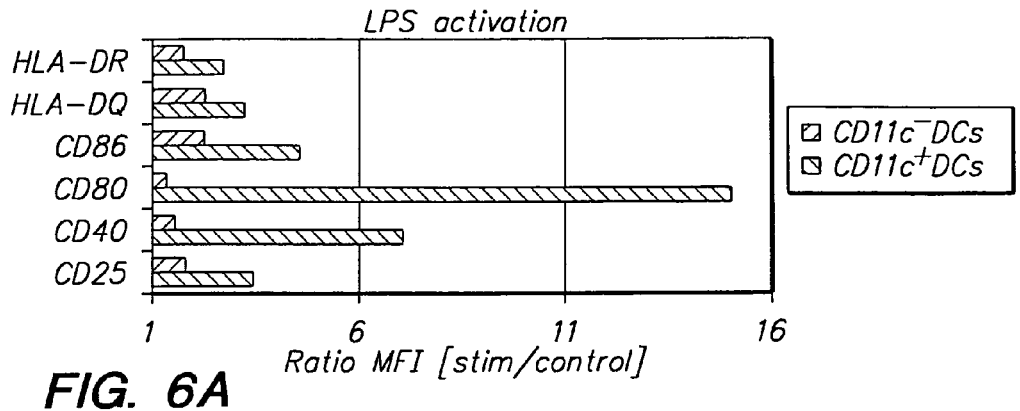
FIGS. 6A-6C is a series of histograms summarizing the effects of three different dendritic activators on the surface expression of the identified markers on peripheral blood dendritic cells in whole blood.
Figure 6B:
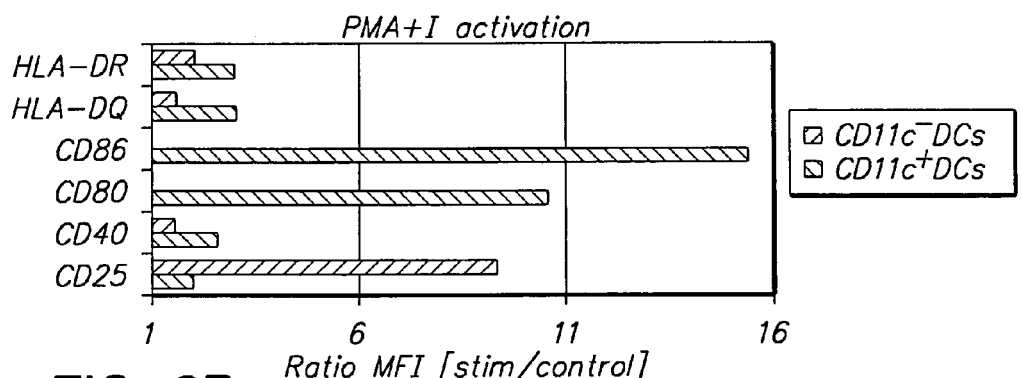
Figure 6C:
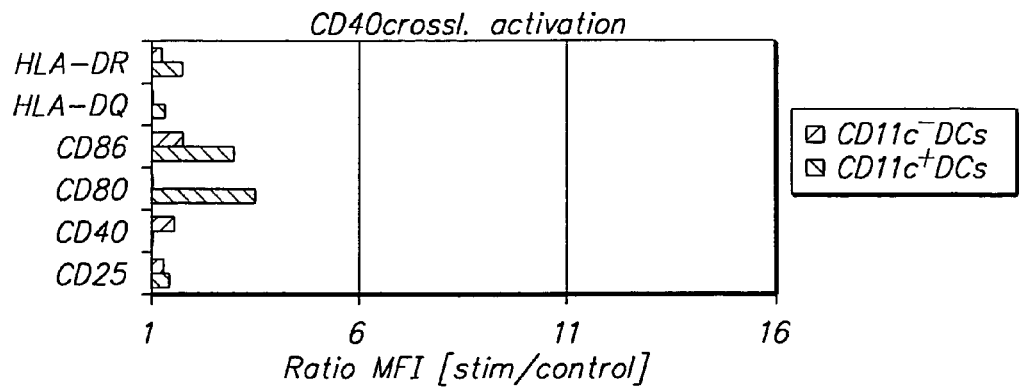

Whole blood samples were drawn from healthy volunteers and activated with LPS, PMA+I, or CD40 crosslinking, in the absence of Brefeldin A, according to the procedures described in Examples 1 and 2. The results are shown in FIG. 6.

As demonstrated in the histograms, the CD11c⁻ subset demonstrated clear upregulation of CD25 expression upon PMA+I activation; upregulation of CD25 was the only distinct response observed in CD11c⁻ subset. In contrast, the CD11c⁻ subset showed upregulation of CD25, CD40, CD80, CD86, HLA-DR and HLA-DQ upon LPS activation. The T cell co-stimulatory molecules, in particular CD80, gave the strongest signal. PMA+I led to an upregulation in CD11c⁺ cells of CD86, CD80, HLA-DQ and HLA-DR. Minimal increase of CD25 and CD40 were observed. Activation via crosslinking of CD40 resulted in increased levels of CD86, CD80, and minimal upregulation of HLA-DR.

Figure 5:
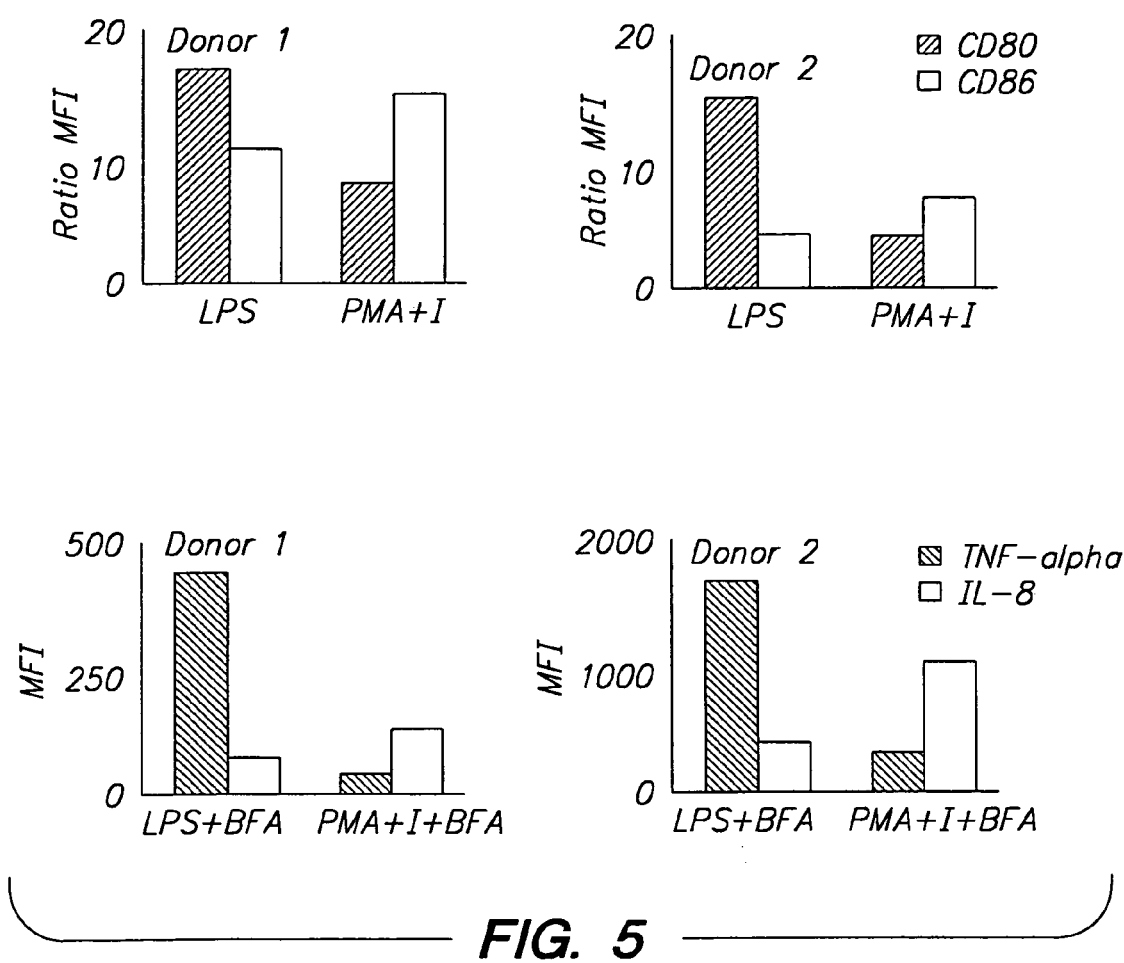
FIGS. 5 presents the differential expression of TNFα and IL-8 in CD11c$^+$ dendritic cells from two donors each activated alternatively with LPS or PMA+I.

FIG. 5 highlights the differences in the TNFα, IL-8, CD80 and CD86 responses of the CD11c⁺ peripheral blood DC subset during activation with PMA+I versus LPS. Two donors are displayed. The expression pattern of cytokines and co-stimulatory molecules varies between different stimuli and is consistent between donors. IL-8 and CD86 are the dominant signal in PMA+I stimulation. In LPS activated samples, TNFα and CD80 are produced to a greater extent.

EXAMPLE 5

Cytokine Kinetic Assay

Whole blood was stimulated with 1 μg/ml LPS and incubated in polypropylene tubes (12×75 mm) at 37° C. in a humidified atmosphere containing 5% $CO_2$. Aliquots were processed, essentially as set forth in Examples 1 and 2 above, every hour from 0 to 8 hrs post stimulation. One hour prior to each sample harvest, BFA was added at 10 μg/mL. Results are shown in FIG. 8.

EXAMPLE 6

Modified Protocols for Whole Blood Flow Cytometric Dendritic Cell Immune Function Assay This Example presents protocols modified slightly from those set forth in Examples 1 and 2; the modified protocols are faster, permit data to be acquired from a greater number of cells, thus improving statistics, and contain fewer aliquoting steps.

DC Surface Antigen Expression in Whole Blood

Response of CD11c⁺ DC to LPS stimulation, reported as the mean fluorescence intensity (mean MFI) of surface expression of the co-stimulatory molecule CD80 or the DC activation marker CD83, is measured as follows.

Materials lipopolysaccharide (LPS), by Sigma, Cat#L2654, 0.5 mg/mL in DMSO, stored at −70° C., working solution is a [1:100] dilution in PBS(1×)

DMSO [1:100] in PBS (1×) (stimulus solvent)

CD11c⁻ APC, by BDIS, Cat#340544, use 15 μL/300 μL whole blood (WB)

lineage cocktail 1 (lin 1) FITC, by BDIS, Cat#340546, 60 μL/300 μL WB

Anti-human HLA-DR PerCP, by BDIS, Cat#347364, use 30 μL/300 μL WB

CD80 PE, by BDIS, Cat#340512, use 60 μL/300 μL WB

CD83 PE, by BDIS (custom conjugate), PC#1520, 50 μg/mL, use 20 μL/300 μL WB

FACS™ lysing Solution 10×, by BDIS, Cat #349202, working solution is a [1:10] dilution in deionized water wash buffer PBS (1×), 0.5% BSA

PBS (1×)

Stimulation Protocol

Add 20 μL of LPS working solution to 1 mL of whole human blood (activated control).

Add 20 μL of DMSO:PBS1× [1:100] to 1 mL of whole human blood (resting control).

Incubate tubes for 4 hrs @ 37° C. and 5% CO2.

Staining Protocol

Perform all steps in 12×75 polypropylene tubes.

add 60 μL lin 1 FITC, 30 μL anti-Hu HLA-DR PerCP, 15 μL CD11c APC and 20 μL CD83 PE or 60 μL CD80 PE add 300 μL whole blood (WB), obtained from the stimulation protocol, vortex incubate for 15 min @ RT in the dark add 3 mL FACSlysing Solution (1×), cap tubes and vortex incubate for 10 min @ RT in the dark pellet (7 min @ 1500 rpm, Sorvall benchtop centrifuge)

aspirate supernatant and vortex to break off pellet add 2 mL wash buffer and vortex pellet (7 min @ 1500 rpm, Sorvall benchtop centrifuge)

aspirate supernatant resuspend stained cells in ~200 μL wash buffer acquire samples (i.e., perform flow cytometric analysis) in ≦1 hr, store samples prior to acquisition @ 4° C.

Note: It is necessary to transfer samples into 12×75 polystyrene tubes for the acquisition; polypropylene tubes do not commonly fit the sample injection system of the flow cytometer. Perform the transfer right before acquisition.

Instrument & Setup & Acquisition Criteria
FACSCalibur Flow Cytometer
4-Color Lyse/Wash (LW) FACSComp software setting
Use a FSC threshold
Acquire the FCS file using anti-human HLA-DR PerCP positive/lin 1 FITC dim events. Use the entire cell suspension for acquisition (about 4,000-7,000 events).
Cell Identification
Scatter low/lin 1 FITC low/anti-human HLA-DR PerCP high/CD11c APC high DC Cytokine Expression in Whole Blood Response of CD11c$^+$ DC to LPS stimulation, reported as mean fluorescence intensity (mean MFI) of TNFα expression in the presence of the Golgi-transport disrupting agent brefeldin A (BFA), is measured as follows. The cells are activated for 2 hrs.

Materials
lipopolysaccharide (LPS), by Sigma, Cat#L2654, 0.5 mg/mL in DMSO, stored at −70° C., working solution is a [1:100] dilution in PBS (1×)
DMSO [1:100] in PBS (1×) (stimulus solvent)
Brefeldin A (BFA), by Sigma, Cat# B-7651, stock solution 50 mg/mL in DMSO, stored at −20° C., working solution [1:100] in PBS(1×), use 20 μL/1 mL WB
CD11c APC, by BDIS, Cat#340544, use 30 μL/300 μL whole blood (WB)
lineage cocktail 1 (lin 1) FITC, by BDIS, Cat#340546, 120 μL/300 μL WB
Anti-human HLA-DR PerCP, by BDIS, Cat#347364, use 60 μL/300 μL WB
Anti-human TNFα PE, by BDIS, Cat#340512, use 20 μL/test
FACS™ Permeabilizing Solution 10×, by BDIS, Cat#340457, working solution is [1:10] dilution in deionized water
FACS™ lysing Solution 10×, by BDIS, Cat#349202, working solution is a [1:10] dilution in deionized water
wash buffer PBS(1×), 0.5% BSA
PBS(1×)
Stimulation Protocol
Add 20 μL of LPS working solution to 1 mL of whole human blood (activated control).
Add 20 μL of DMSO:PBS1× [1:100] to 1 mL of whole human blood (resting control).
Then add 20 μL of BFA working solution to both control tubes.
Incubate tubes for 2 hrs @ 37° C. and 5% $CO_2$.
Staining Protocol (Intracellular)
Perform all steps in 12×75 polypropylene tubes.
add 120 μL lin 1 FITC, 60 μL anti-Human HLA-DR PerCP, 30 μL CD11c APC
add 300 μL whole blood (WB), obtained from the stimulation protocol, vortex
incubate for 15 min @ RT in the dark
add 3 mL FACS lysing Solution 1×, cap tubes and vortex
incubate for 10 min @ RT in the dark
pellet (7 min @ 1500 rpm, Sorvall benchtop centrifuge)
aspirate supernatant and vortex gently to break off pellet
resuspend in 1 mL FACS permeabilizing Solution 1×
incubate @ RT for 10 min in the dark
add 2.5 mL wash buffer, cap tubes and vortex gently
pellet (10 min @ 1500 rpm, Sorvall benchtop centrifuge)
decant supernatant
resuspend permeabilized cell pellet gently in remaining supernatant
add 20 μL anti-human TNFα PE reagent for intracellular staining
incubate for 30 min @ RT in the dark
add 2 mL wash buffer and gently vortex
pellet (10 min @ 1500 rpm, Sorvall benchtop centrifuge)
decant supernatant
resuspend stained and permeabilized cells in ~200 μL wash buffer
acquire sample in ≦1 hr, store samples prior to acquisition @ 4° C.

Note: It is necessary to transfer samples into 12×75 polystyrene tubes for the acquisition; polypropylene tubes do not commonly fit the sample injection system of the flow cytometer. Perform the transfer right before acquisition.

Instrument & Setup & Acquisition Criteria
FACSCalibur Flow Cytometer.
4-Color Lyse/No Wash (LNW) setting in FACSComp software.
Use a FSC threshold.
Acquire the FCS file using anti-human HLA-DR PerCP positive/lin 1 FITC dim events. Use the entire cell suspension for acquisition (4,000-7,000 events).
Cell Identification
Scatter low/lin 1 FITC low/Anti-human HLA-DR PerCP high/CD11c APC high.

All patents, patent publications, and other published references mentioned herein are hereby incorporated by reference in their entirety as if each had been individually and specifically incorporated by reference herein.

While preferred illustrative embodiments of the present invention are described, it will be apparent to one skilled in the art that various changes and modifications may be made therein without departing from the invention, and it is intended in the appended claims to cover all such changes and modifications which fall within the true spirit and scope of the invention.

What is claimed is:

1. A flow cytometric method for measuring dendritic cell function in whole blood, comprising:
   (a) contacting a whole blood sample with a dendritic cell activator;
   (b) adding to said sample a plurality of dendritic cell-distinguishing antibodies, a dendritic cell subsetting antibody that is an antibody specific for CD11c or an antibody specific for CD123, and at least one antibody specific for a dendritic cell surface marker indicative of activation, wherein said antibodies are fluorophore-conjugated;
   (c) lysing red blood cells in said sample; and then
   (d) flow cytometrically assaying said sample for binding of said antibody specific for said dendritic cell surface activation marker by dendritic cells of a dendritic cell subset, wherein the pattern of binding of the dendritic cell-distinguishing antibodies and the dendritic cell subsetting antibody identifies dendritic cells of the dendritic cell subset, and the level of binding of the antibody specific for a dendritic cell surface marker provides a measure of dendritic cell function.

2. The method of claim 1, wherein said surface marker indicative of dendritic cell activation is selected from the group consisting of CD25, CD40, CD80, CD83, CD86, CMRF-441 CMRY-56, and HLA-DQ.

3. The method of claim 1, wherein said dendritic cell activator is selected from the group consisting of lipopolysaccharide (LPS), phorbol 12-myristate 13 acetate plus ionomycin (PMA+I) and a CD4-crosslinker.

4. The method of claim 3, wherein said dendritic cell activator is LPS.

5. The method of claim 3, wherein said dendritic cell activator is PMA+I.

6. The method of claim 3, wherein said dendritic cell activator is a CD40 crosslinker.

7. The method of claim 1, wherein at least one of said plurality of dendritic cell distinguishing antibodies is specific for a non-dendritic cell lineage.

8. The method of claim 7, wherein each of said nondendritic cell lineage-specific antibodies is specific for an antigen selected from the group consisting of CD3, CD14, CD16, CD19, CD20, and CD56.

9. The method of claim 8, wherein said plurality of dendritic cell distinguishing antibodies are collectively specific for CD3, CD 14, CD16, CD19, CD20 and CD56.

10. The method of claim 9, wherein all of said nondendritic cell lineage-specific antibodies are conjugated to an identical fluorophore.

11. The method of claim 10, wherein said fluorophore is fluorescein isothiocyanate (FITC).

12. The method of claim 1, wherein said plurality of dendritic cell-distinguishing antibodies includes an antibody specific for HLA-DR.

13. The method of claim 1, wherein said plurality of dendritic cell-distinguishing antibodies includes an antibody specific for CD4.

14. The method of claim 1, wherein said dendritic cell subsetting antibody is specific for CD11c.

15. The method of claim 1, wherein said dendritic cell subsetting antibody is specific for CD123.

* * * * *